(12) United States Patent
Cowan et al.

(10) Patent No.: US 7,670,315 B2
(45) Date of Patent: Mar. 2, 2010

(54) INJECTORS, INJECTOR SYSTEMS AND METHODS FOR INJECTING FLUIDS

(75) Inventors: Kevin P. Cowan, Allison Park, PA (US); David M. Reilly, Pittsburgh, PA (US); Joseph J. Fularz, Lower Burrell, PA (US); Paul J. Swartz, Uniontown, PA (US); Mark Trocki, Cheswick, PA (US); David A. Mishler, Slippery Rock, PA (US)

(73) Assignee: Medrad, Inc., Indianola, PA (US)

( * ) Notice: Subject to any disclaimer, the term of this patent is extended or adjusted under 35 U.S.C. 154(b) by 839 days.

(21) Appl. No.: 11/336,150

(22) Filed: Jan. 21, 2006

(65) Prior Publication Data

US 2006/0184124 A1 Aug. 17, 2006

Related U.S. Application Data

(60) Provisional application No. 60/645,939, filed on Jan. 21, 2005.

(51) Int. Cl.
*A61M 37/00* (2006.01)
*A61M 5/00* (2006.01)

(52) U.S. Cl. .......... 604/155; 604/154; 600/432

(58) Field of Classification Search .......... 604/131, 604/151, 154, 155, 890.1, 891.1; 128/DIG. 1, 128/DIG. 12; 600/432
See application file for complete search history.

(56) References Cited

U.S. PATENT DOCUMENTS

| 3,949,746 A | * | 4/1976 | Wallach ............ 604/152 |
|---|---|---|---|
| 4,006,736 A | | 2/1977 | Kranys et al. |
| 4,677,980 A | | 7/1987 | Reilly et al. |
| 5,006,112 A | | 4/1991 | Metzner |
| 5,034,004 A | | 7/1991 | Crankshaw |
| 5,176,646 A | * | 1/1993 | Kuroda ............ 604/154 |
| 5,383,858 A | | 1/1995 | Reilly et al. |
| 5,494,036 A | | 2/1996 | Uber, III et al. |
| 5,807,334 A | | 9/1998 | Hodosh et al. |
| RE37,602 E | | 3/2002 | Uber, III et al. |
| 6,575,856 B2 | | 6/2003 | Anderson |

FOREIGN PATENT DOCUMENTS

WO 02082113 10/2002

OTHER PUBLICATIONS

U.S. Appl. No. 10/916,946, Griffiths et al., filed Aug. 12, 2004.
U.S. Appl. No. 10/921,083, Callen et al., filed Aug. 18, 2004.

(Continued)

*Primary Examiner*—Nicholas D Lucchesi
*Assistant Examiner*—Nathan R Price
(74) *Attorney, Agent, or Firm*—James R. Stevenson; Henry E. Bartony, Jr.

(57) ABSTRACT

An injector for injection a fluid into a patient, including: a first pressurizing mechanism adapted to operatively connect with a first fluid container to pressurize fluid therein; at least a second pressurizing mechanism to operatively connect with a second fluid container to pressurize a fluid therein; a single drive; and a transmission to control how power from the drive is distributed to the first pressurizing mechanism of the first container and to the second pressurizing mechanism of the second container to control injection of fluid from the first container and from the second container. The drive can, for example, be an electric motor or other drive.

24 Claims, 21 Drawing Sheets

OTHER PUBLICATIONS

Keeler, E.K., et al., "Accessory Equipment Considerations with Respect to MRI Compatibility," JMRI, 8, 1 (1998).

Lemieux, L., et al., "Recording of EEG During MRI Experiments: Patient Safety," MRM, 38, 943 (1997).

"A Primer on Medical Device Interactions with Magnetic Resonance Imaging Systems," U.S. Food and Drug Administration Center for Devices and Radiological health (Feb. 7, 1997).

* cited by examiner

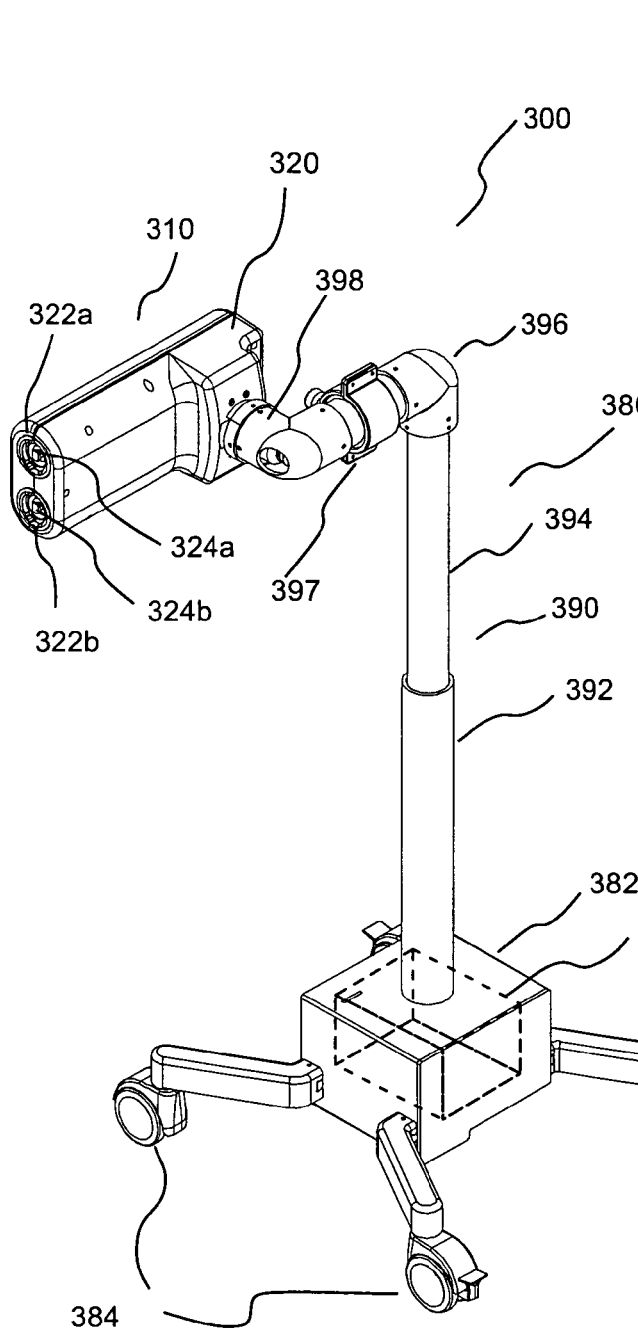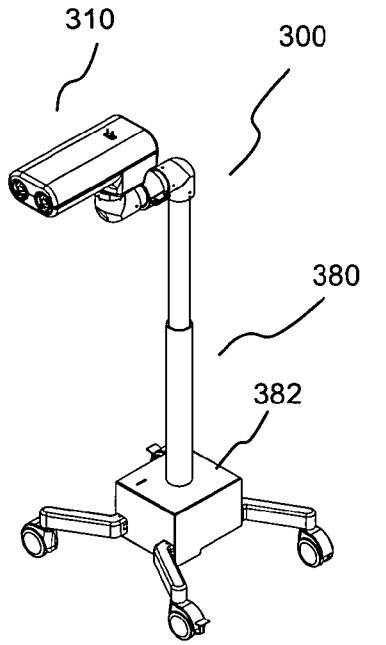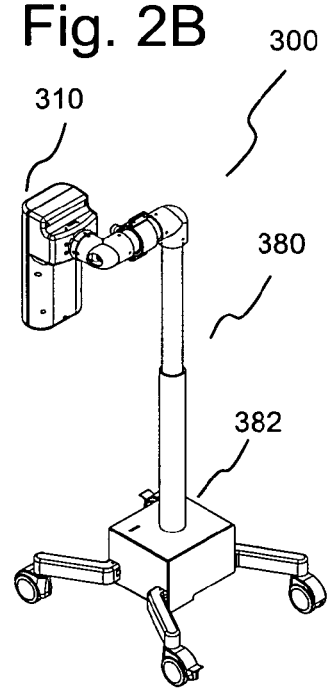
Fig. 2A
Fig. 2B
Fig. 2C

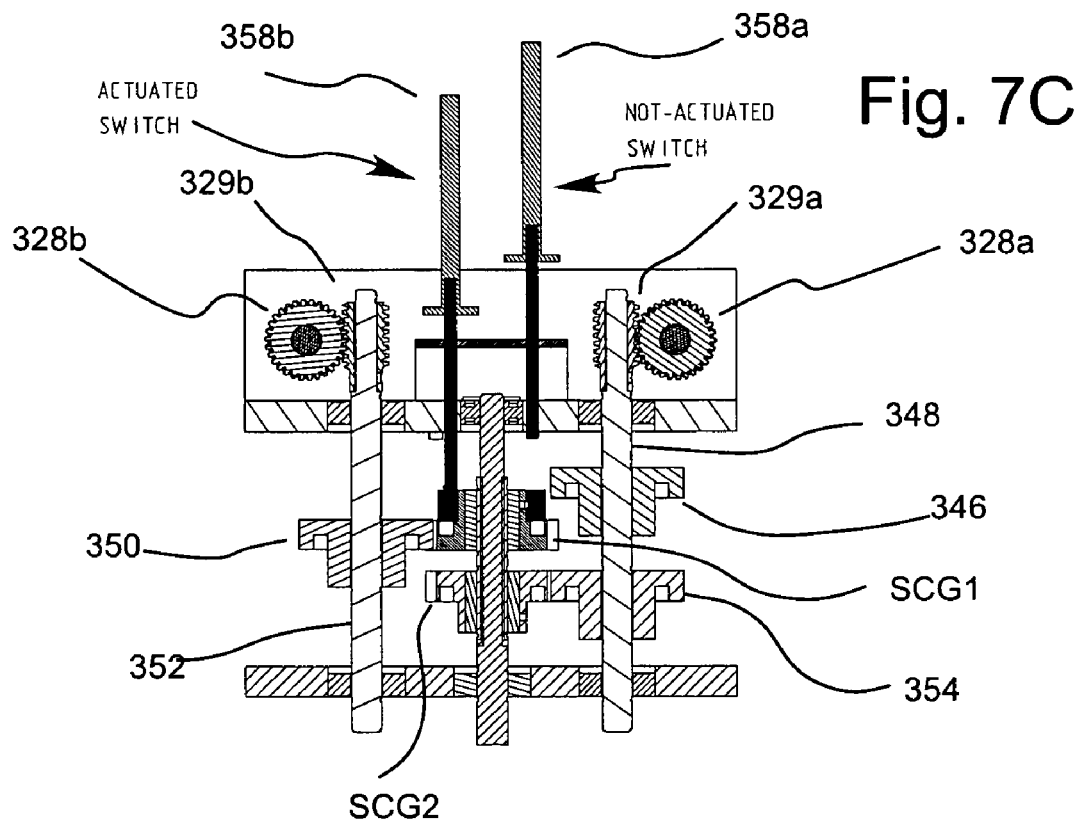
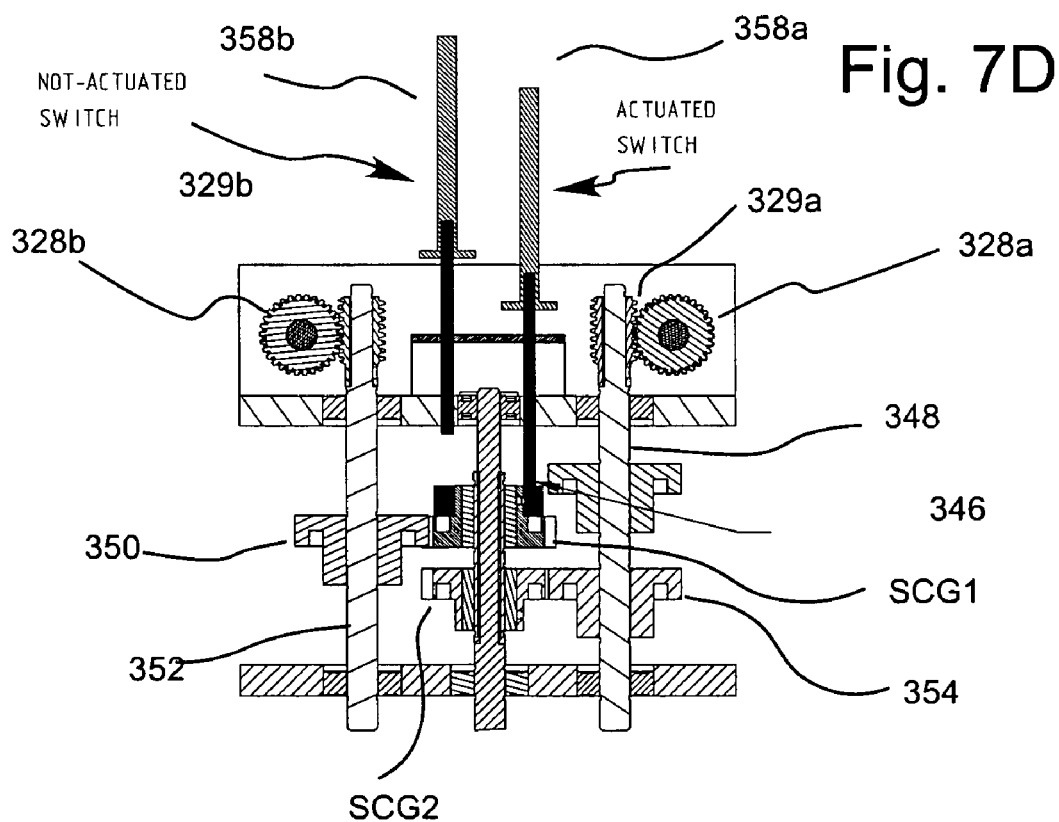

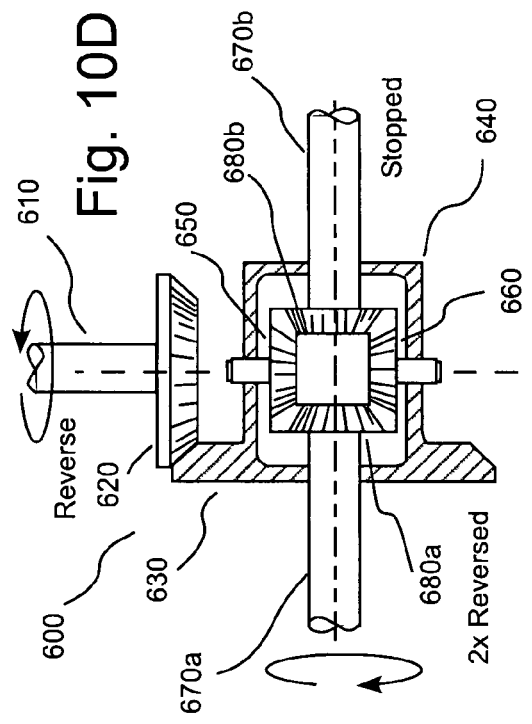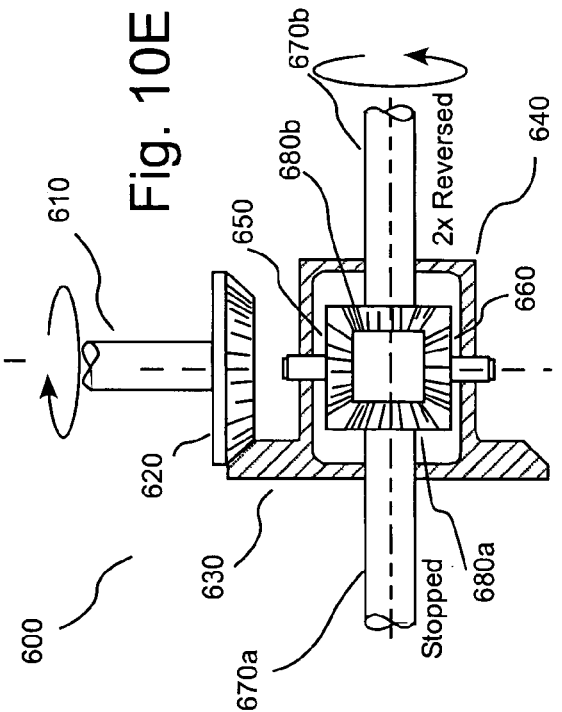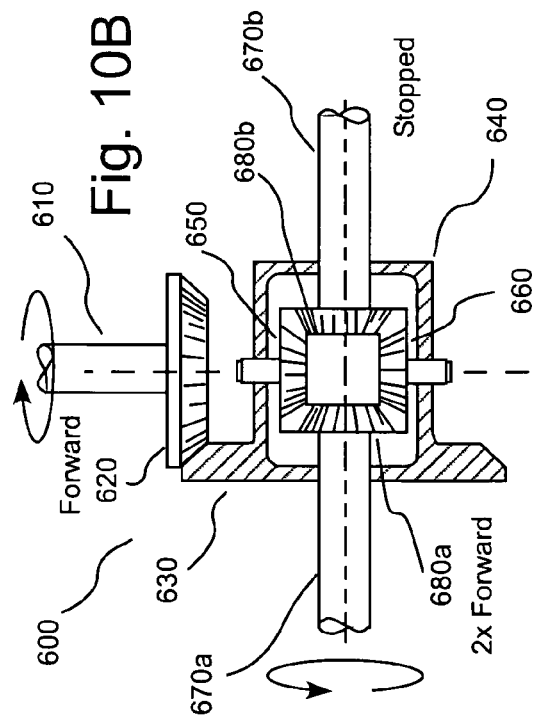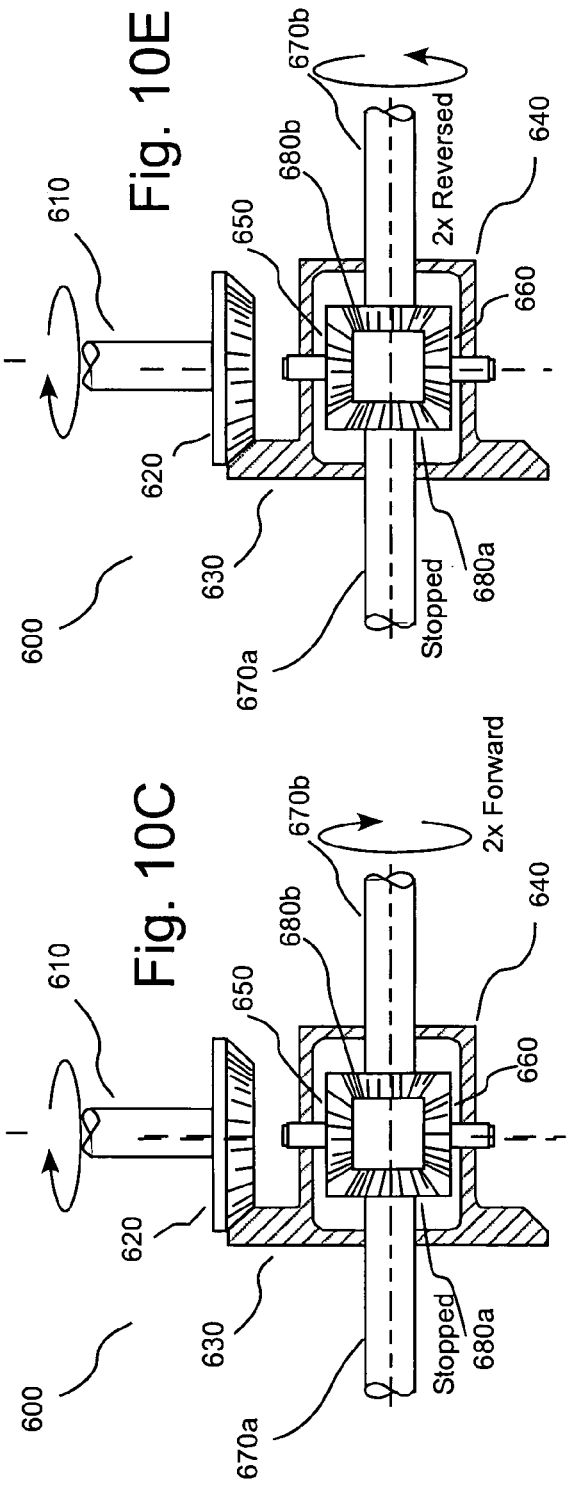

Fig. 13A
PRIOR ART
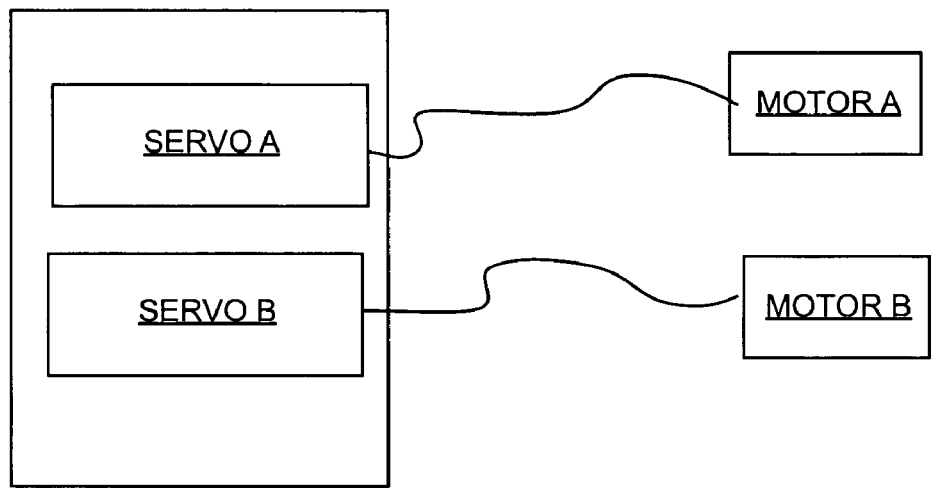
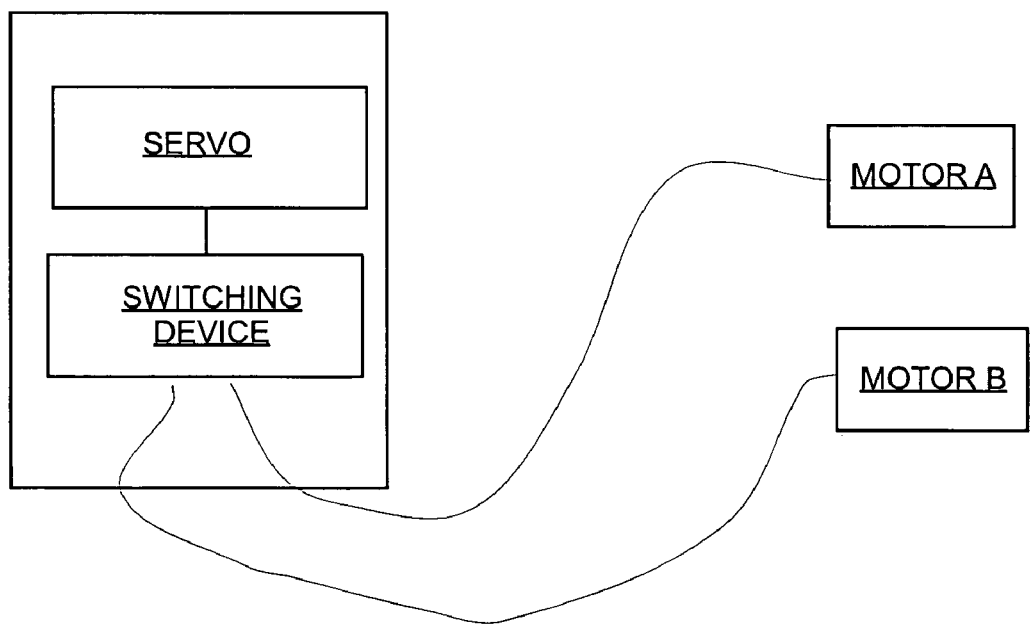
Fig. 13B

INJECTORS, INJECTOR SYSTEMS AND METHODS FOR INJECTING FLUIDS

CROSS-REFERENCE TO RELATED APPLICATION

The present application claims the benefit of U.S. Provisional Patent Application Ser. No. 60/645,939, filed Jan. 21, 2005, the disclosure of which is incorporated herein by reference.

BACKGROUND OF THE INVENTION

The present invention relates generally to injectors, injector systems and methods of injecting fluids, and, especially, to injectors, injector systems and methods of injecting fluids into a patient (that is, into either a human or a so called lower animal).

In many medical procedures, such as drug delivery, it is desirable to inject a fluid into a patient. Likewise, numerous types of contrast media (often referred to simply as contrast) are injected into a patient for many diagnostic and therapeutic imaging procedures. For example, contrast media are used in diagnostic procedures such as X-ray procedures (including, for example, angiography, venography and urography), computed tomography (CT) scanning, magnetic resonance imaging (MRI), and ultrasonic imaging. Contrast media are also used during therapeutic procedures, including, for example, angioplasty and other interventional radiological procedures.

A number of injector-actuated syringes and powered injectors for use in medical procedures such as angiography, computed tomography (CT), ultrasound and NMR/MRI have been developed. U.S. Pat. No. 4,006,736, for example, discloses an injector and syringe for injecting fluid into the vascular system of a human being or an animal. Typically, such injectors comprise drive members such as pistons that connect to a syringe plunger. The drive members are in operative connection with an electric motor, which is controlled to control the reciprocal motion of the drive member. For example, U.S. Pat. No. 4,677,980, the disclosure of which is incorporated herein by reference, discloses an angiographic injector and syringe wherein the drive member of the injector can be connected to, or disconnected from, the syringe plunger at any point along the travel path of the plunger via a releasable mechanism. A front-loading syringe and injector system is also disclosed in U.S. Pat. No. 5,383,858, the disclosure of which is incorporated herein by reference.

Dual-syringe injectors such as the SPECTRIS® available from Medrad, Inc. of Indianola, Pa. are commercially available (see, for example, U.S. Reissue Pat. No. 37,602). In imaging procedure, dual-syringe injectors can, for example, enable the sequential or simultaneous injection of a contrast medium and a diluent of flushing fluid such as saline. The diluent or flushing fluid can, for example, be used to control concentration of the contrast injected or to facilitate injection of a bolus of contrast medium having desirable characteristics (for example, a well defined or tight bolus). In such dual-syringe injectors, a separate drive member or piston is provided for each syringe/syringe plunger. In turn, a separate motor and associated control circuitry and logic are provided for each motor.

Currently available injectors, and particularly, dual-syringe injectors can be quite complex and expensive to manufacture. Moreover, the nature of the MR environment can substantially increase the cost of injectors designed for use therein. In that regard, for use in an MR environment, the components of an injector are preferably fabricated from materials that are non-magnetic and/or otherwise suitable or compatible for use in an MRI environment. A review of issues related to the compatibility of various equipment in an MRI environment is set forth in Keeler, E. K. et al., "Accessory Equipment Considerations with Respect to MRI Compatibility," *JMRI*, 8, 1 (1998), the disclosure of which is incorporated herein by reference. See also, Lemieux, L. et al., "Recording of EEG During MRI Experiments: Patient Safety," *MRM*, 38, 943 (1997); and "A Primer on Medical Device Interactions with Magnetic Resonance Imaging Systems," U.S Food and Drug Administration—Center for Devices and Radiological Health (Feb. 7, 1997), the disclosures of which are incorporated herein by reference.

Furthermore, electric actuators such as DC brush motors, step motors, brushless DC motors or other wound coil motors and solenoids often fail in a strong magnetic field as a result of damage to internal permanent magnets. Moreover, currents induced within the field windings of such devices from electromagnetic fields can cause overheating and potential damage to the windings and any connected electronic circuitry. The MRI magnetic field can also interfere with the device created magnetic field and prevent accurate operation.

Furthermore, differences in magnetic permeability of materials within the actuator and eddy currents induced within actuator windings can affect the homogeneity or uniformity of the MRI magnetic field, generating image artifacts. Actuators that use mechanical commutation, such as DC brush motors, can also generate radio frequency energy during switching which can induce unwanted artifacts upon the acquired MRI images. Specialized shielding and specialized materials are typically required in manufacturing injectors for use in MR environments.

For the above reasons and others, it is desirable to develop improved injectors, injectors systems and methods for injecting fluids into patients, and particularly, to develop injectors that are less complex and/or less expensive to manufacture than currently available injectors.

SUMMARY OF THE INVENTION

In one aspect, the present invention provides an injector for injecting a fluid into a patient, including: a first pressurizing mechanism adapted to operatively connect with a first fluid container to pressurize fluid therein; at least a second pressurizing mechanism to operatively connect with a second fluid container to pressurize a fluid therein; a single drive; and a transmission to control how power from the drive is distributed to the first pressurizing mechanism of the first container and to the second pressurizing mechanism of the second container to control injection of fluid from the first container and from the second container. The drive can, for example, be an electric motor or other drive.

The transmission can, for example, be a mechanical transmission with no active electronic actuators. The transmission can be fabricated from MR compatible components. The transmission can, for example, include a movable gear selector, a Sprague clutch gear or a one way clutch gear system, a moving gear, a differential gear system or a continuously variable transmission. The transmission can also include a movable gear selector to select one of a plurality of gears to be driven In several embodiments, the first fluid container is a first syringe and the first pressurizing mechanism is a first drive member adapted to operatively connect with a first plunger slidably disposed within the first syringe. The second fluid container can be a second syringe and the second pressurizing mechanism can be a second drive member adapted to operatively connect with a second plunger slidably disposed within the second syringe. The first drive member can be in operative connection with a first ball screw that is adapted to be in operative connection with the single drive (for example, a motor). The second drive member can be adapted to be in operative connection with a second ball screw that is in operative connection with the single drive (for example, a motor).

The first drive member can be placed in connection with the transmission via a first worm gear. The second drive member can also be placed in connection with the transmission via a second worm gear. In certain embodiments, at least one brake system (for example, an electromagnetic brake system or a mechanical abutting break system such as a break gear system, a pawl system, a ratchet system or a friction system) can be provided to prevent rearward movement of at least one of the first drive member and the second drive member when the at least one of the first drive member and the second drive member is not being moved by the transmission.

In one embodiment, the drive is connected to a first rigid drive shaft. The first rigid drive shaft is in operative connection with a flexible transfer mechanism for transferring power from the first rigid drive shaft at a first end of the flexible transfer mechanism. The flexible transfer mechanism is in operative connection with a second rigid drive shaft at a second end of the flexible transfer mechanism. The flexible transfer mechanism can, for example, include a belt. The flexible transfer mechanism can further include a first pulley in operative connection with the first rigid drive shaft and a second pulley in operative connection with the second rigid drive shaft. The first pulley is operatively connected with the second pulley by the belt. The flexible transfer mechanism can also include a bevel gear and shaft. In one embodiment, the flexible transfer mechanism is no greater than 18 inches in length. In another embodiment, the flexible transfer mechanism is no greater than 12 inches in length.

The first rigid drive shaft can include a first rigid drive shaft member and a second rigid drive shaft member. The second rigid drive shaft member can be telescopically connected to the first rigid drive shaft member so that the length of the first rigid drive shaft can be adjusted. In this embodiment, the first pulley is in operative connection with the second rigid drive shaft member. The flexible transfer mechanism can also include a flex shaft.

In one aspect, an injector of the present invention such as described above includes a transmission that includes at least one movable driving element to control how power from the drive is distributed to the first pressurizing mechanism of the first container and to the second pressurizing mechanism of the second container. The at least one movable driving element can, for example, be a movable gear that is movable to at least a first position in which it is in operative connection with the first pressurizing mechanism and to at least a second position in which it is in operative connection with the second pressurizing mechanism. The moveable gear can linearly movable between the first position and the second position (for example, upon a shaft). The moveable gear can also rotatable about an axis between the first position and the second position.

The moveable gear can be movable to at least a third position in which it is in operative connection with first pressurizing mechanism and in operative connection with the second pressurizing mechanism.

The transmission can include a drive gear in operative connection with the moveable gear. The moveable gear can be rotatable about the axis of the drive gear while remaining in operative connection with the drive gear to the first position and to the second position.

The at least one moveable drive element can also be a gear selector that is movable to at least a first position in which it causes rotation of a first gear that is in operative connection with the first pressurizing mechanism and is moveable to at least a second position in which it causes rotation of a second gear that is in operative connection with the second pressurizing mechanism. In one embodiment, the gear selector is linearly movable within a bore of a driving shaft. The driving shaft has at least a first driving gear and a second driving gear thereon. The first driving gear and the second driving gear are spaced in position on the driving shaft and are rotatable about the shaft until being activated by the gear selector. The first driving gear is in operative connection with the first gear and the second driving gear is in operative connection with the second gear. The gear selector activates the first driving gear in the first position so that the first driving gear rotates with a rotation speed of the driving shaft, and the gear selector activates the second driving gear in the second position so that the first driving gear rotates with a rotation speed of the driving shaft.

In one embodiment, the gear selector is linearly movable within the driving shaft to at least a third position in which it activates a third driving gear on the driving shaft. The third driving gear is spaced in position on the shaft from the first driving gear and the second driving gear. The third driving gear is rotatable about the shaft until being activated by the gear selector. The third driving gear is in operative connection with a third gear that is in operative connection with the first pressurizing mechanism and a fourth gear that is in operative connection with the second pressurizing mechanism.

The gear selector can, for example, include an abutment member that protrudes through a passage in the driving shaft to contact at least one corresponding abutment member on the first driving gear in the first position and to contact at least one corresponding abutment member on the second gear in the second position.

In another aspect, an injector of the present invention such as described above includes a transmission comprises at least a first continuously variable transmission element so that power from the drive is distributable to at least one of the first pressurizing mechanism or the second pressurizing mechanism in a generally continuously variable manner. The injector first continuously variable transmission element can, for example, adapted to be placed in operative connection with the first pressurizing mechanism so that power from the drive is distributable to the first pressurizing mechanism in a generally continuously variable manner. The transmission can further include a second continuously variable transmission element that is adapted to be placed in operative connection with the second pressurizing mechanism so that power from the drive is distributable to the second pressurizing mechanism in a generally continuously variable manner. The injector can further include a controlling linkage between the first continuously variable transmission element and the second continuously variable transmission element so that a generally constant total flow can be maintained.

In one embodiment, the first continuously variable transmission element includes a first conical torque input member and the second continuously variable transmission element comprises a second conical torque output member, the second conical member that is oriented with respect to the first conical member such that the axis of rotation of the second conical member is parallel to the axis of rotation of the first conical member and wherein a smaller diameter end of the second conical member is adjacent a larger diameter end of the first conical member. Input torque from the drive can, for example, be transferred from the first conical member to the second conical member by an endless belt mechanism (for example, a belt or a chain) in operative connection with the first conical member and the second conical member. The belt mechanism is movable along the axes of the first conical member and the second conical member.

In another aspect, an injector of the present invention such as described above operates such that reversal of the motion of the drive causes power to be shifted from the first pressurizing mechanism to the second pressurizing mechanism.

In one embodiment, the transmission includes at least a first one way clutch gear in operative connection with a drive shaft. The drive shaft is in operative connection with the drive. The first one way clutch gear id driven by the drive shaft upon rotation of the drive shaft in a first direction and slipping upon rotation of the drive shaft in a second direction, opposite to the first direction.

The transmission further include at least a second one way clutch gear in operative connection with the drive shaft. The second one way clutch gear is driven by the drive shaft upon rotation of the drive shaft in the second direction and slips upon rotation of the drive shaft in the first direction. The first one way clutch gear is spaced from the second one way clutch gear on the drive shaft. The first one way clutch gear and the second one way clutch gear can, for example, be linearly movable on the drive shaft.

In one embodiment, when the first one way clutch gear and the second one way clutch gear are in a first position on the drive shaft, the first one way clutch gear is in operative connection with a first gear which is in operative connection with a the first pressurizing mechanism and the second one way clutch gear is in operative connection with a second gear which is in operative connection with the second pressurizing mechanism. When the first one way clutch gear and the second one way clutch gear are in a second position on the drive shaft, the first one way clutch gear is in operative connection with the second gear and the second one way clutch gear is in operative connection with a third gear which is in operative connection with the first pressurizing mechanism. The first gear and the third gear rotate about the same axis/shaft. Rotation of the first gear or the third gear can, for example, rotate a first worm gear shaft upon which the first gear and the second gear are positioned, and rotation of the second gear can rotate a second worm gear shaft upon which the second gear is positioned.

The injector can further include at least one switching system operable to change the position of the first one way clutch gear and the second one way clutch gear on the drive shaft between the first position and the second position. The switching system can include a signal communicator adapted to send a signal to the drive to control a direction of rotation of the drive shaft to correspond to a state of the switching system.

The switching system can, for example, include a first reverse switch operable when actuated to place the first one way clutch gear and the second one way clutch gear in the second position on the drive shaft. The signal communicator can be adapted to send a signal to the drive, upon actuation of the first reverse switch, to cause rotation of the drive shaft in a first direction to cause rearward motion of the first pressurizing mechanism. The switching system can also include a second reverse switch operable when actuated to position the first one way clutch gear and the second one way clutch gear in the second position on the drive shaft. The signal communicator is adapted to send a signal to the drive, upon actuation of the second reverse switch, to cause rotation of the drive shaft in the second first direction to cause rearward motion of the second pressurizing mechanism.

In another aspect, the present invention provides an injector for injecting a fluid into a patient, including: at least a first drive member adapted to operatively connect with a first plunger of a first syringe and a drive system operatively connectible with the first drive member via a first worm gear such that rearward force on the first plunger within the first syringe cannot drive the first worm gear in reverse and thereby retract the first drive member. The injector can further include: at least a second drive member adapted to operatively connect with a second plunger of a second syringe and a second worm gear in operative connection between the drive system and the second drive member such that rearward force on the second plunger within the second syringe cannot drive the second worm gear in reverse and thereby retract the second drive member.

In another aspect, the present invention provides an injector for injecting a fluid into a patient, including: at least a first drive member adapted to operatively connect with a first plunger of a first syringe; a drive system operatively connectible with the first drive member; and a first brake system operatively connectible to the first drive member such that a rearward force on the first plunger within the first syringe cannot retract the first drive member when the drive system is not advancing the first drive member. The brake system can, for example, include a pawl, a braking gear, a ratchet system, an electromagnetic brake, a friction brake, a disc brake and/or other brake system as known in the mechanical arts. The injector can further include: at least a second drive member adapted to operatively connect with a second plunger of a second syringe and a second brake system operatively connectible with the second drive member such that a rearward force on the second plunger within the second syringe cannot retract the second drive member when the drive system is not advancing the second drive member.

In other aspects of the present invention, the pitch of one or more lead screws can be chosen to prevent backdrive of a non-driven drive member. Likewise, certain gearing systems such a sprague gears can provide prevention of backdrive of non-driven gears.

In a further aspect, the present invention provides an injector for injecting a fluid into a patient, including: at least a first drive member adapted to operatively connect with a first plunger of a first syringe; and a drive system operatively connectible with the first drive member. The drive system is connected to a first rigid drive shaft. The first rigid drive shaft is in operative connection with a flexible transfer mechanism for transferring power from the first drive shaft at a first end of the flexible transfer mechanism. The flexible transfer mechanism is in operative connection with a second rigid drive shaft at a second end of the flexible transfer mechanism. The second rigid drive shaft is operatively connectible to the first drive member.

In still a further embodiment, the present invention provides an injector for injection a fluid into a patient, including: a first pressurizing mechanism adapted to operatively connect with a first fluid container to pressurize fluid therein; at least a second pressurizing mechanism to operatively connect with a second fluid container to pressurize a fluid therein; a first drive operatively connectible to the first pressurizing mechanism; a second drive operatively connectible to the second pressurizing mechanism; and a single control mechanism to control how power from the first drive is transferred to the pressurizing mechanism of the first container and how power from the second drive is transferred to the pressurizing mechanism of the second container to control injection of fluid from the first container and the second container. The control mechanism can, for example, be a servo mechanism that is switchable from being in connection with the first drive to being in connection with the second drive.

In still another embodiment, the present invention provides an injector comprising a variable speed transmission. The variable speed transmission includes a drive shaft that can be driven via various gear ratios. The transmission can, for example, provide for different speeds in a forward and in a reverse direction as well as for multiples speeds in either or both direction.

In one embodiment, the injector includes a transmission having at least one moveable gear selector that is movable to at least a first position in which it causes rotation of a first gear that is in operative connection with the drive shaft and is moveable to at least a second position in which it causes rotation of a second gear that is in operative connection with drive shaft. The first gear and the second gear can have different diameters.

In one embodiment, the gear selector can, for example, be linearly movable within a bore of the drive shaft. The first gear and a second gear can be spaced in position on the drive shaft and can be rotatable about the drive shaft until being activated by the gear selector. The gear selector can activate the first gear in the first position so that the first gear rotates with a rotational speed of the drive shaft, and the gear selector can activate the second gear in the second position so that the second gear rotates with the rotational speed of the driving shaft.

In one embodiment, the gear selector includes an abutment member that protrudes through a passage in the drive shaft to contact at least one corresponding abutment member on the first gear in the first position and to contact at least one corresponding abutment member on the second gear in the second position.

The injector can further include a power source (for example, a motor) adapted to rotate a power shaft. An axis of the power shaft can be parallel to the axis of the drive shaft. The power shaft can, for example, have a first powering gear thereon in operative connection with the first gear and have a second powering gear thereon in operative connection with the second gear. The first powering gear and the second powering gear can have different diameters.

The present invention also provides injector systems including the injectors of the present invention. Such injector systems can, for example, comprise one or more syringes attachable to the injectors. The present invention also provides methods of injecting one or more fluids (sequentially and/or simultaneously) using the injectors or components of the injectors of the present invention.

BRIEF DESCRIPTION OF THE DRAWINGS

Other aspects of the invention and their advantages will be discerned from the following detailed description when read in connection with the accompanying drawings, in which:

FIG. 2A illustrates a perspective view of an embodiment of an injector of the present invention with the injector head in a first orientation.

FIG. 2B illustrates a perspective view of an embodiment of an injector of the present invention with the injector head in a second orientation.

FIG. 2C illustrates a perspective view of an embodiment of an injector of the present invention with the injector head in a third orientation.

FIG. 7C illustrates front view of the transmission of FIG. 7A with the second reverse swatch activated.

FIG. 7D illustrates front view of the transmission of FIG. 7A with the first reverse swatch activated.

FIG. 10B illustrates rotation of the shafts associated with the differential transmission of FIG. 10A, wherein the drive shaft is rotated in a forward direction to drive a first shaft in a forward direction while a second shaft is stopped or braked.

FIG. 10C illustrates rotation of the shafts associated with the differential transmission of FIG. 10A, wherein the drive shaft is rotated in a forward direction to drive the second shaft in a forward direction while the first shaft is stopped or braked.

FIG. 10D illustrates rotation of the shafts associated with the differential transmission of FIG. 10A, wherein the drive shaft is rotated in a reversed direction to drive the first shaft in a reversed direction while the second shaft is stopped or braked.

FIG. 10E illustrates rotation of the shafts associated with the differential transmission of FIG. 10A, wherein the drive shaft is rotated in a rearward direction to drive the second shaft in a reversed direction while the first shaft is stopped or braked.

FIG. 13A illustrates an embodiment of prior art two motor system system including two servos.

FIG. 13B illustrates an embodiment of a two motor system of the present invention including a single servo and a servo switching device.

DETAILED DESCRIPTION OF THE INVENTION

In several representative embodiments of the present invention described below, use of the injectors of the present invention in an MR environment is discussed. One skilled in the art appreciates that the injectors, injector systems and methods for injection fluids of the present invention are widely applicable to any type of procedure in which a fluid is injected into a patient. Moreover, several representative embodiments of the present invention are described in which fluid is injected from syringes by driving plungers of syringes using drive members of an injector. One skilled in the art appreciates that the principles of the present invention are applicable to pressurization and injection of fluid from other type of containers or chambers using other types of drives or actuators, for example, peristaltic pumps, gear pumps, rotary pumps, positive displacement pumps or multiple in-line syringe pumps.

Figure 1A:
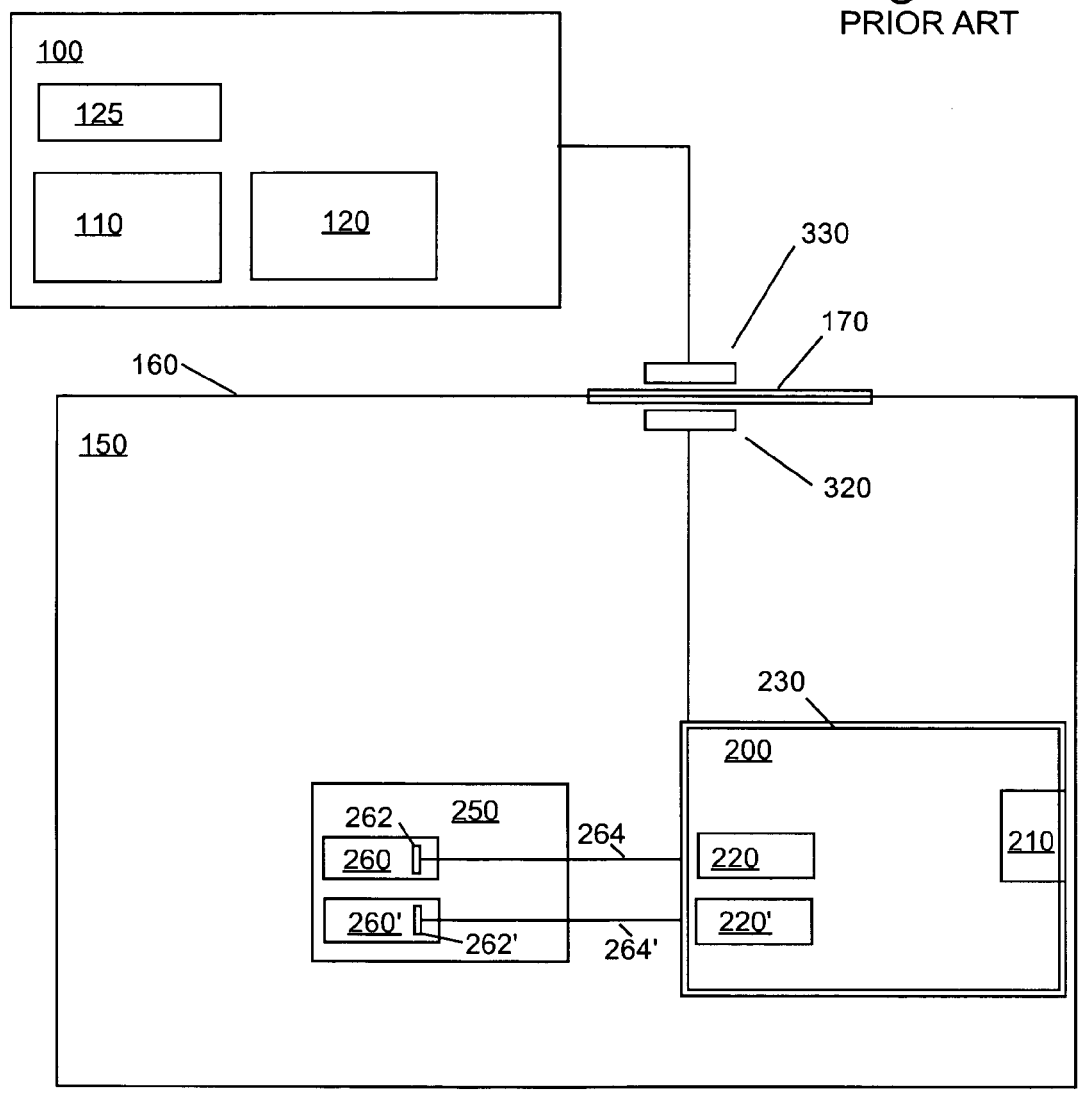
FIG. 1A illustrates a schematic diagram of a currently available injector system.
Figure 1B:
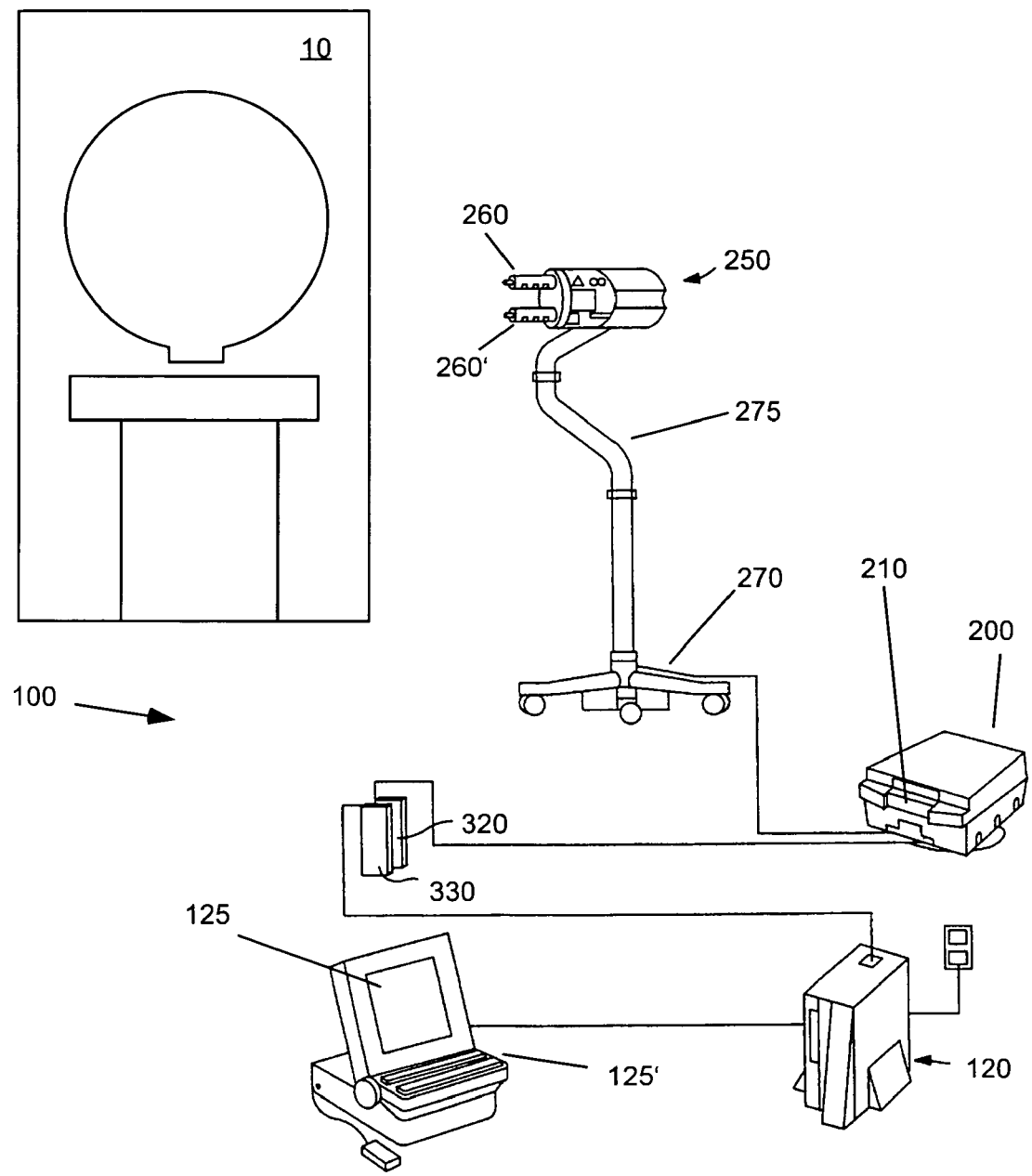
FIG. 1B illustrates another diagram of the injector system of FIG. 1A.
Figure 3:
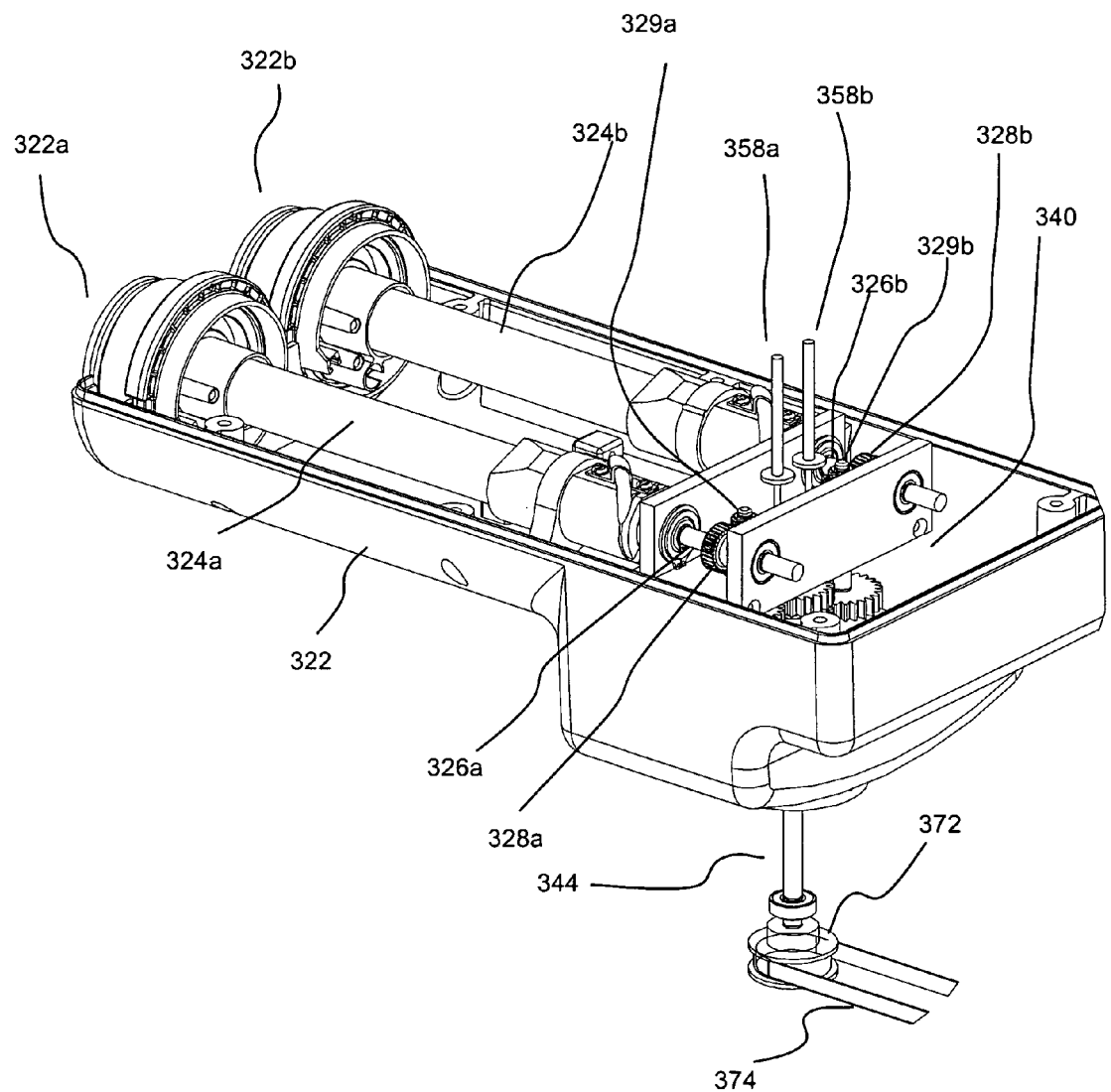
FIG. 3 illustrates a perspective view of the injector head of FIG. 2A with part of the housing removed.
Figure 4:
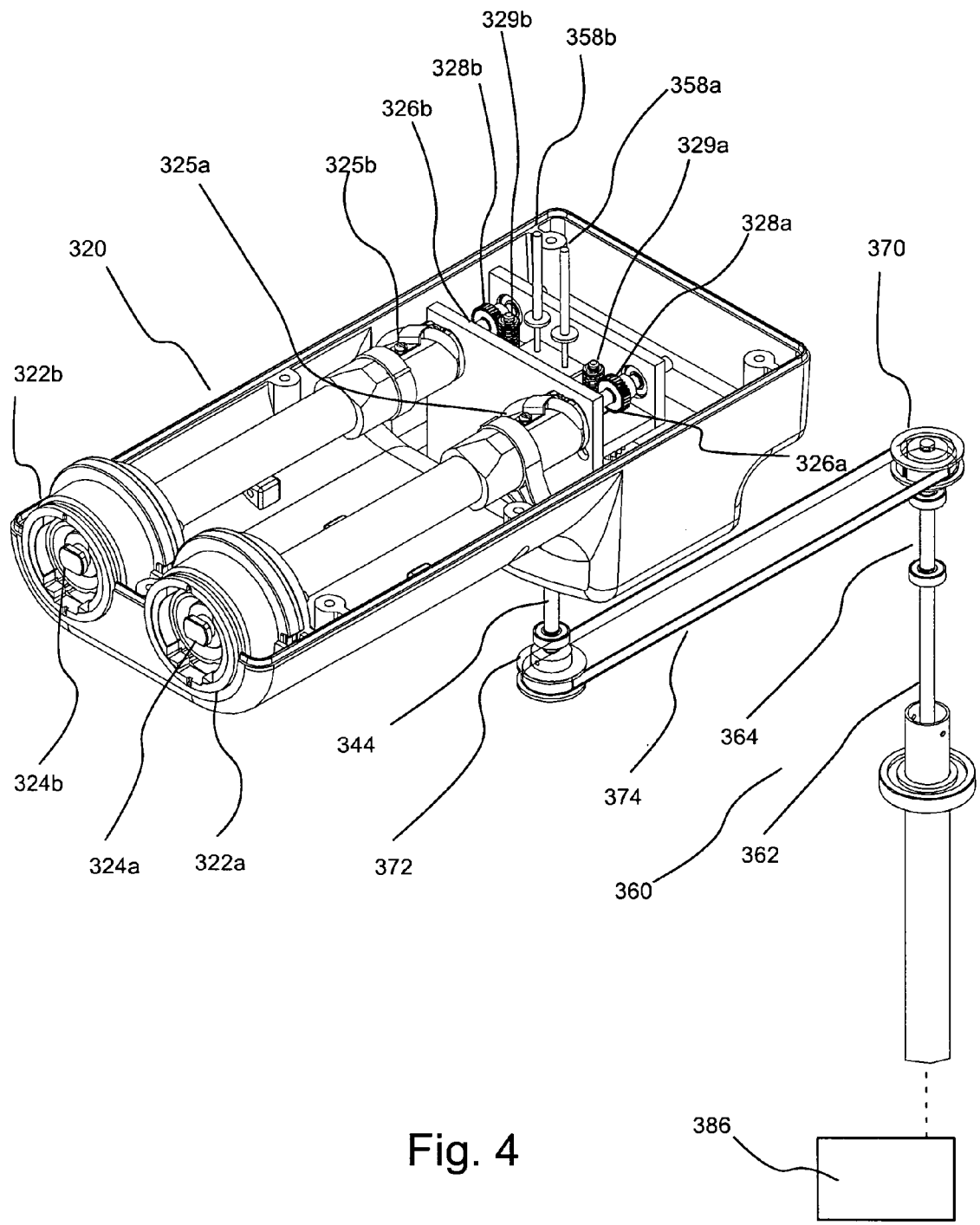
FIG. 4 illustrates another perspective view of the injector head of FIG. 2A with part of the housing removed as well as a portion an embodiment of a drive transfer system of the present invention.
Figure 5:
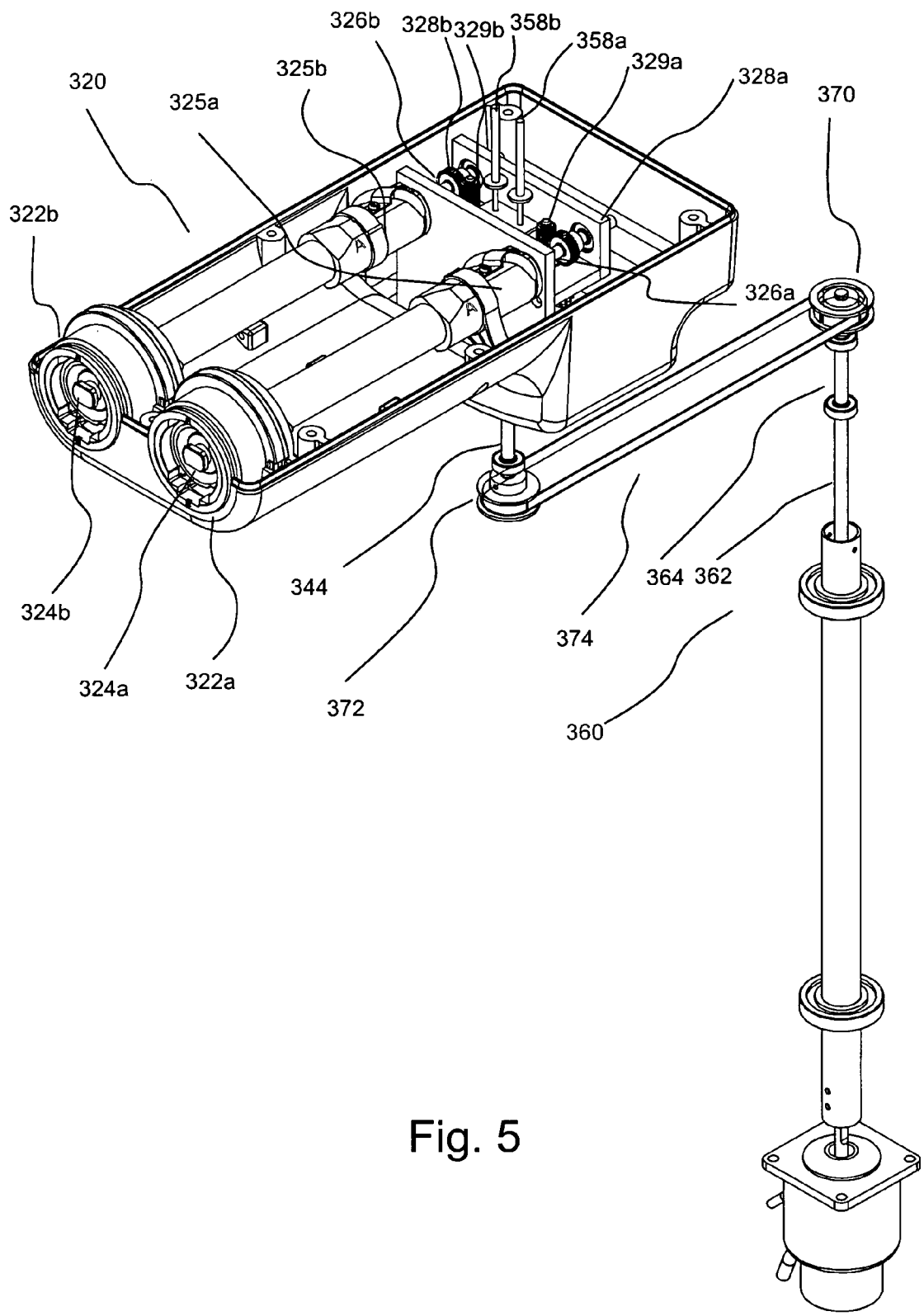
FIG. 5 illustrates another perspective view of the injector head of FIG. 2A with part of the housing removed and the drive transfer system of FIG. 4.
Figure 6:
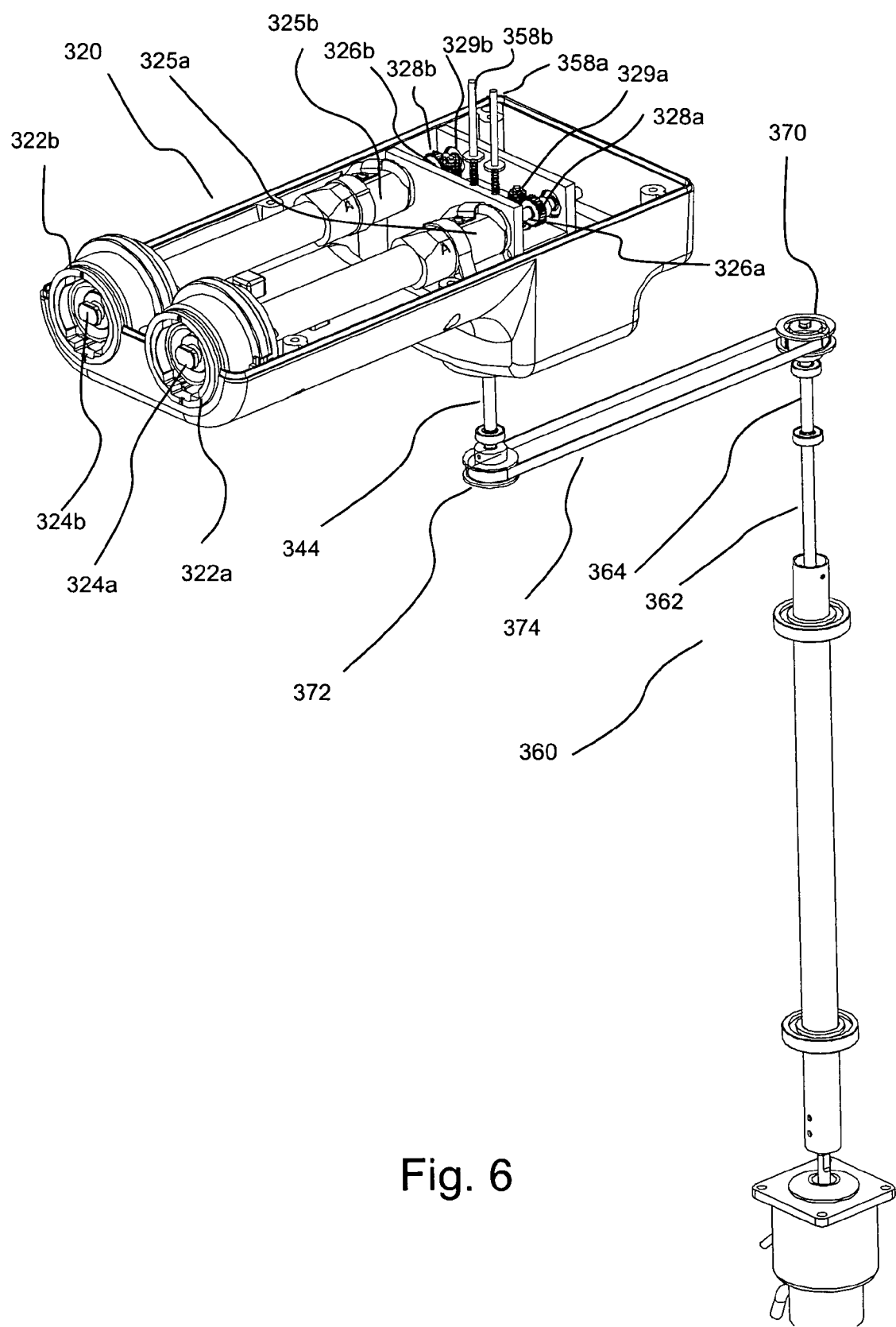
FIG. 6 illustrates another perspective view of the injector head of FIG. 2A with part of the housing removed and the drive transfer system of FIG. 4.

FIGS. 1A and 1B illustrate a SPECTRIS® injector system for use in a magnetic resonance imaging environment with magnetic imaging system 10, which is currently available from Medrad, Inc. of Indianola, Pa, the Assignee of the present application. One embodiment of the injector system of FIGS. 1A and 1B is described in U.S. Pat. No. RE 37,602, assigned to the Assignee of the present invention, the disclosure of which is incorporated herein by reference. The system includes an external system controller 100 that preferably includes a processing unit 110 (for example, a digital microcomputer), a battery charger 120 and an operator interface 125 (including, for example a data entry unit 125' and a display 125"). System controller 100 is located outside of a shielded area such as an imaging room 150 that is shielded from electromagnetic interference by, for example, a shield 160. Electromagnetic isolation can, for example, be achieved by completely enclosing the room with copper sheet material or some other suitable, conductive layer such as wire mesh.

Shielded imaging room 150 can, for example, include a patient viewing window 170 in shield 160 to allow an observer and/or operator to view the room without breaching electromagnetic shield 160. Window 170 can, for example, be formed by sandwiching a wire mesh material (not shown) between sheets of glass or by coating the window with a thin coating of conductive material such as gold (not shown) to maintain the continuity of electromagnetic shield 160.

The system also includes a contrast media injection control unit 200 located within shielded imaging room 150. Injection control unit 200 can, for example, be powered by a rechargeable battery 210. Injection control unit 200 can, for example, include control circuitry which controls electric motors 220 and 220', which are preferably located within injection control unit 200. Injection control unit 200 can be contained within an electromagnetic shield 230 to reduce or eliminate any undesired electromagnetic radiation generated by electric motors 220 and 220' from interfering with the magnetic field used to generate the magnetic resonance image.

In general, separation of the electric motors from the injection head 250, as well as the additional electromagnetic shielding, results in improved system performance and improved overall image quality. Injection control unit 200 can, for example, be separated (for example, by ten to fifteen feet) from injection head unit 250, which is typically placed near imaging system 10 and near the patient. As illustrated in FIG. 1B, injection head unit 250 is mounted on a mobile base unit 270 via a connecting member 275.

During an injection, injection head unit 250 is preferably located in close proximity to the patient to decrease the distance that the contrast media fluid must travel from the contrast media from syringes 260 and 260' (or other fluid chambers) connected to injection head unit 250. Injection head unit 250 further includes drive members 262 and 262' such as pistons that act to pressurize the contents of syringes 260 and 260', respectively, for injection into the patient. Drive members 262 and 262' are connected to electric motors 220 and 220', respectively, in injection control unit 200 by a non-rigid connection such as by flexible mechanical drive shafts 264 and 264', respectively. Drive shafts 264 and 264' can, for example, made from a nonferrous metal such as hard brass.

For control of injection head unit 250 by system controller 100, communication is maintained between system controller 100 and injection control unit 200. For example, injector control unit 200 can be in communication with a communication unit 320. Likewise, control system 100 can be in communication with a communication unit 330. Communication units 320, 330 can, for example, communicate across viewing window 170 using light energy as disclosed in U.S. Pat. No. 5,494,036.

Currently available injectors for use in the injector systems of FIGS. 1A and 1B, although having excellent functionally, are rather complex to manufacture and likewise relatively expensive. The present inventors have discovered that both complexity and cost can be reduced in a dual-syringe injector by driving both pistons using a single drive.

In that regard, FIGS. 2A through 8, illustrate an embodiment of an injector 300 that can operate in the injector system of FIGS. 1A and 1B in place of the injector illustrated therein. Injector 300 includes an injector head 310 supported upon a mobile injector stand 380. Mobile injector stand 380 includes a base 382 to which casters 384 are attached as known in the art. A support 390 is attached to base 382. In the embodiment of FIGS. 2A through 8, support 390 includes a generally vertical (in the orientation of FIGS. 2A through 2C, for example) member 392. A second vertical member 394 is telescopically attached to first vertical member 392 at a first end of second vertical member 394. A 90° or elbow coupling 396 is attached to second vertical member 394 at a second end thereof. A horizontal (in the orientation of FIGS. 2A through 2C, for example) member 397 is also attached to coupling 396 at a first end of horizontal member 397. A second 90° or elbow coupling 398 is attached to horizontal member 397 at a second end thereof. Second 90° or elbow coupling 398 is attached to injector head 310. As illustrated in a comparison of FIGS. 2A and 2B, second coupling 398 is rotatably connected to horizontal member 397 so that the orientation of injector head 310 can be rotated 90° about the axis of horizontal member 397.

As illustrated in a comparison of FIGS. 2A and 2C, injector head 310 is rotatably connected to coupling 398. Injector head 310 can, for example, be rotated to a downward orientation as illustrated in FIG. 2C, wherein the syringes (not shown) attached thereto are oriented downward. As known in the art, in this position, fluid can be injected from the syringes with a reduced likelihood of injection of air. Injector head 310 can also be rotated about coupling 398 approximately 180° from the orientation of FIG. 2C so that injector head 310 and the syringes (not shown) attached thereto are oriented upward. In this position, as known in the art, the syringe can be loaded so that any air in the syringes remains at the front of the syringe, thereby simplifying purging of that air from the syringes.

Injector head 310 includes a housing 320. A forward wall of housing 320 includes a first syringe retaining mechanism 322a for removable attachment of a first syringe (not shown) and a second syringe retaining mechanism 322b for removable attachment of a second syringe (not shown). Syringes are attached to syringe retaining mechanisms 322a and 322b via, for example, a bayonet connection as described, for example, in U.S. Pat. No. 5,383,858, assigned to the assignee of the present invention, the disclosure of which is incorporated herein by reference. Other syringe retaining mechanisms (and associated adapters) as known in the art can also be used. A first drive member 324a, which operably attaches to the plunger of the first syringe as in the SPECTRIS Injector available from Medrad, Inc., is movable in a reciprocal manner through the opening of first retaining mechanism 322a. A second drive member 324b, which operably attaches to the plunger of the second syringe as in the SPECTRIS Injector available from Medrad, Inc., is movable in a reciprocal manner through the opening of second retaining mechanism 322b.

As illustrated, for example, in FIG. 3-6, in the embodiment of FIGS. 2A through 8, drive members 324a and 324b are connected to ball screws 326a and 326b, respectively. A gear 328a of first ball screw 326a is in operative connection with a first worm gear 329a via a ball screw shaft 326a. A gear 328b of second ball screw 326b is in operative connection with a second worm gear 329b via a ball screw shaft 326b. In the embodiment of FIGS. 2 through 8, the rotation of worm gears 329a and 329b (and thereby motion of drive members 324a and 324b, respectively) is controlled by a mechanical transmission 340, which is in operative connection with a single drive (for example, motor 386 or other rotational drive) in mobile support base 382. Drives other that electric motors (for example, hydraulic, pneumatic etc.) can also be used. Drive mechanisms and actuators suitable for use in MR environments are described in U.S. patent application Ser. No. 10/916,946 (filed Aug. 12, 2004) and Ser. No. 10/921,083 (filed Aug. 18, 2004), assigned to the assignee of the present invention, the disclosures of which are incorporated herein by reference.

Use of a mechanical transmission such as transmission 340 to control the translation of energy from single motor 386 to one or both of drive members 324a and 324b can, for example, provide benefits for use of injector 300 in an MR environment. In that regard, specialized materials and/or shielding are often required in the case of electroactuators commonly used in the control architecture of currently available injector heads, raising both the price and complexity of such injector heads. Mechanical transmissions used in the present invention (which can be constructed with no active electronics) are readily constructed from MR compatible materials (for example, nonferrous materials including, but not limited to, a polymeric materials and certain metals).

In general, MR compatible materials, mechanisms, actuators and MR compatible devices are capable of operation in an MRI environment without significant reduction in performance and without significant effect upon the MRI procedure.

Figure 7A:
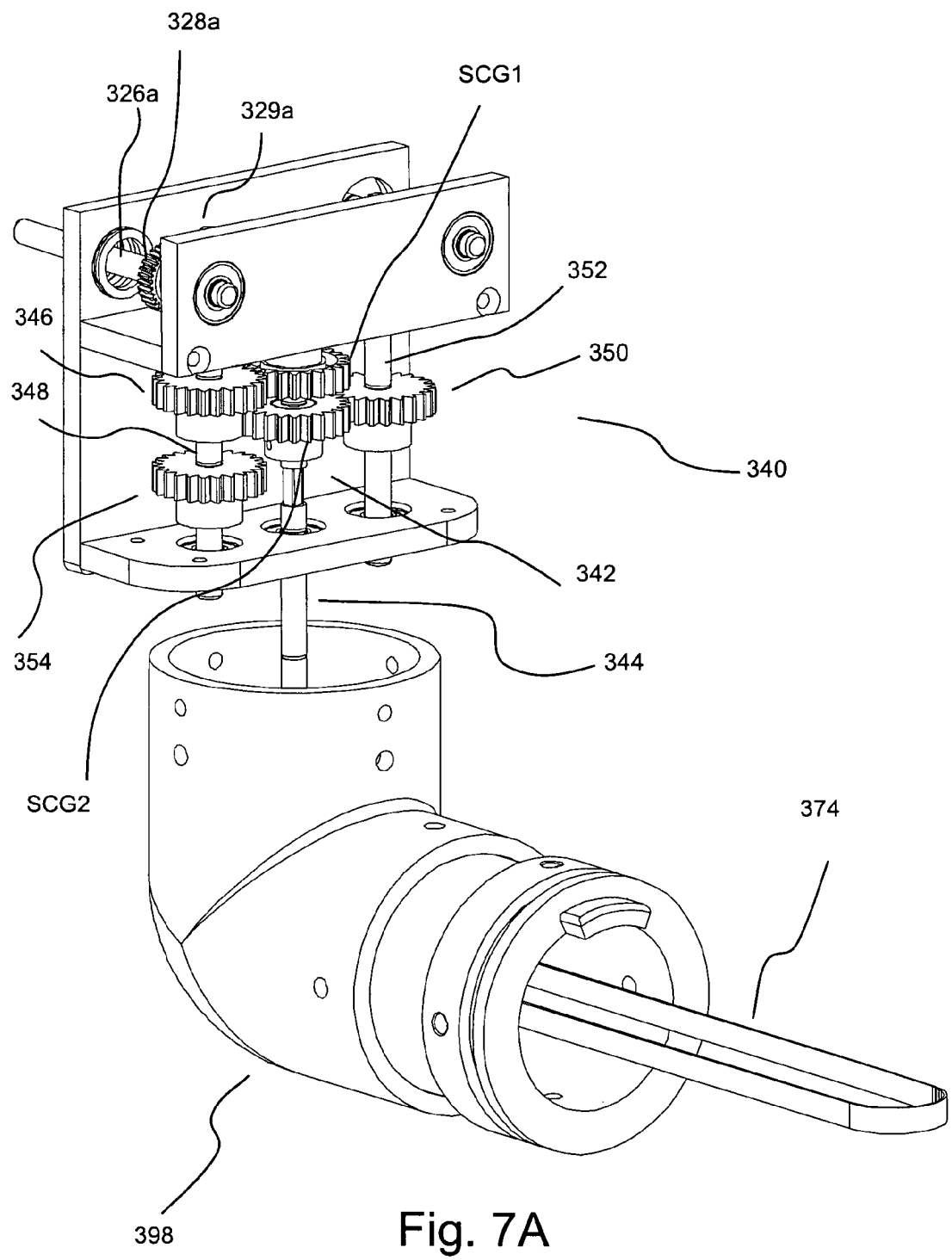
FIG. 7A illustrates a perspective view of an embodiment of a transmission of the present invention.
Figure 7B:
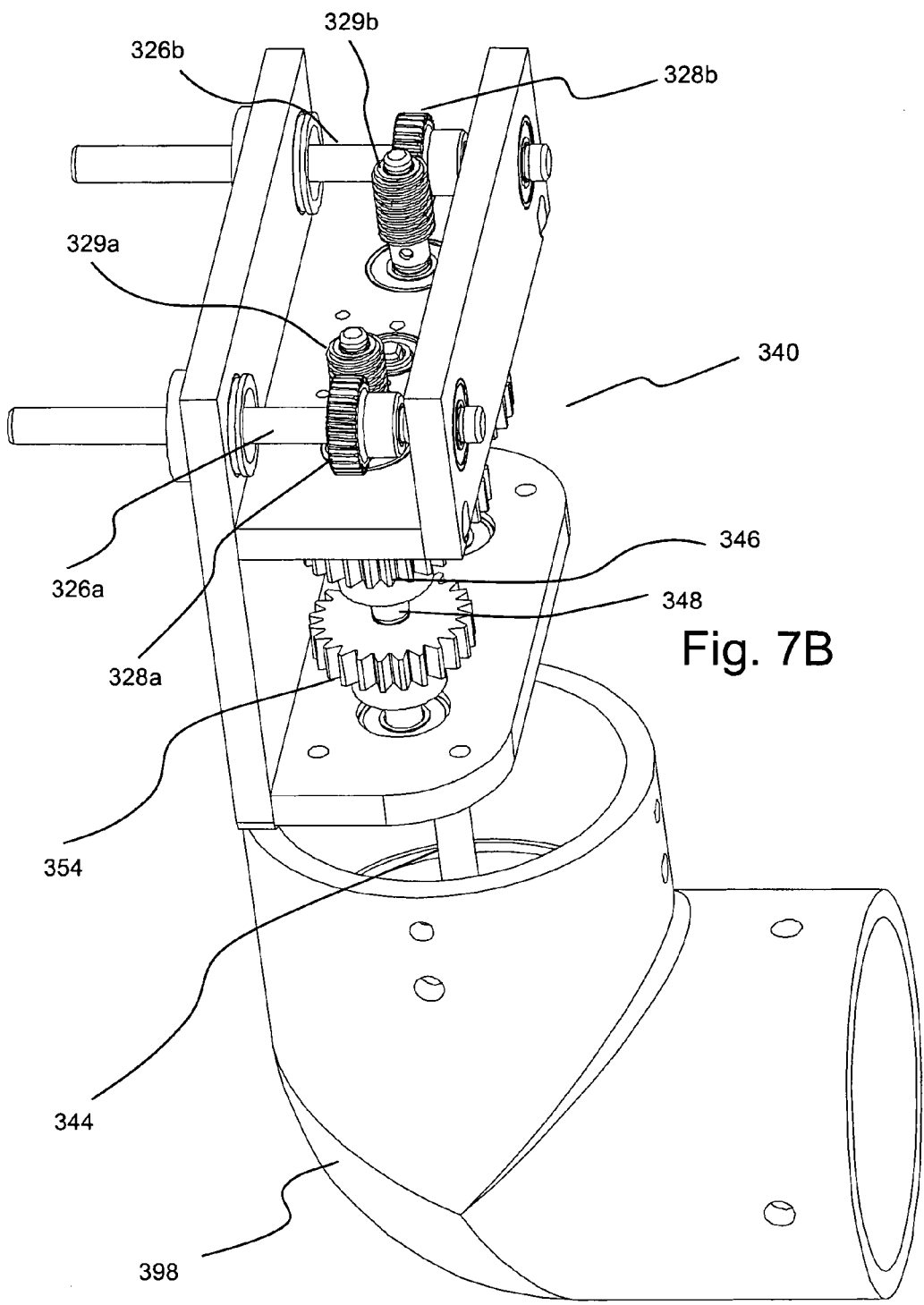
FIG. 7B illustrates another perspective view of the transmission of FIG. 7A.

An embodiment of mechanical transmission 340 is illustrated, for example, in FIGS. 7A and 7B. In this embodiment, a one-way clutch or Sprague clutch system 342 is used. In this system; a first Sprague clutch gear SCG1 and a second Sprague clutch gear SCG2 are placed in opposite operational directions and are either driven or slip, depending on the direction of rotation of a rigid drive shaft 344, which is in operative connection with motor 386. The direction of rotation of drive shaft 344 is determined by the direction of rotation of motor 386.

As motor 386 and thereby drive shaft 344 are rotated in a clockwise direction, gear SCG1 is engaged and causes rotation of drive gear 346, which is in operative connection with worm gear 329a via shaft 348, causing worm gear 329a to rotate to advance drive member 324a through rotation of gear 328a and connected ball screw 326a. Gear SCG2 is not driven as the slip clutch is in the non-driven direction. Thus, worm gear 329b is not driven and drive member 324b does not move. Moreover, drive member 324b cannot be driven back by system pressure because of the connection of gear 328b with worm gear 329b.

When motor 386 and drive shaft 344 are rotated in a counter-clockwise direction, gear SCG1 is not driven as its slip clutch is now in the non-driven direction. Thus, worm gear 329a is not driven, and drive member 324a does not move. Drive member 324a cannot be driven back by system pressure because of the connection of gear 328a with worm gear 329a. As drive shaft 344 is rotated in the counterclockwise direction, gear SCG2 is engaged and causes rotation of drive gear 350, which is in operative connection with worm gear 329b via shaft 352, causing worm gear 329b to rotate to advance drive member 324b through rotation of gear 328b and connected ball screw 326b.

To effect reverse motion or retraction of drive member 324a, an operator first presses reverse button/actuator 358a (see, for example, FIGS. 3, 7C and 7D), causing gears SCG1 and SCG2 to drop down one gear position so that gear SCG1 is aligned to be in operative connection with drive gear 350 and gear SCG2 is aligned to be in operative connection with drive gear with drive gear 354. Pressing reverse button 358a also sends a signal to motor 386 to rotate in a counterclockwise direction, thereby driving gear SCG2. Drive gear 354 is thereby caused to rotate in a direction opposite to the direction in which drive gear 346 was driven in the above description of forward motion of drive member 324a. Rotation of shaft 348 causes worm gear 329a to be driven in a reverse direction, thereby causes retraction of drive member 324a. Gear SCG1 is not driven. Thus, drive gear 350 is not driven and drive member 324b does not move.

To effect reverse motion of drive member 324b, an operator first presses reverse button/actuator 358b (see, for example, FIG. 3), causing gears SCG1 and SCG2 to drop down one gear position so that gear SCG1 is aligned to be in operative connection with drive gear 350 and gear SCG2 is aligned to be in operative connection with drive gear with drive gear 354 as described above. Pressing reverse button 358b also sends a signal to motor 386 (and thus drive shaft 342) to rotate in a clockwise direction. Gear SCG2 remains idle in the direction of rotation of drive shaft 344. Gear SCG1 rotates, causing drive gear 350, and thereby worm gear 329b, to rotate in a reverse direction to retract drive member 324b. Gear SCG2 remains idle and drive member 324a does not move.

As briefly described above, worms gears 329a and 329b can drive gear 328a and 328b, respectively, in a forward or reverse direction, but worm gears 329a and 329b cannot be driven by gears 328a and 328b as a result of the relatively a steep ramp and reduction. The inability to drive worm gears 329a and 329b eliminates the chance for the non-driven drive member to be driven back by pressure in the operatively connected syringe. Recoil caused, for example, by a rubber cover of the syringe plunger being compressed at the tip of the syringe and resulting aspiration is also prevented. Moreover, there is no need to hold an idle drive member motor locked as typically required in currently available dual-syringe injectors, which results in a relatively large energy drain, which could be an issue on battery systems. Prevention of retraction of a non-driven drive member can also result in a tighter bolus than possible in injectors in which such retraction is possible when a syringe plunger is under a rearward load.

In the illustrated embodiment, worms gears 329a and 329b are on opposite sides of ball screw gears 328a and 328b, respectively, (in other words, as one looks down on ball screw gears 328a and 328b, worm gears 329a and 329b are both on the inside). Thus, when worm gear 328a rotates counterclockwise it will advance drive member 324a. When worm gear 329b rotates clockwise, it advances drive member 324b. Thus, the same thread (right hand or left hand) ball screw can be used for each of drive members 324a and 324b. This result can also be accomplished by positioning both of worm gears 329a and 329b on the outside of ball screw gears 328a and 328b, respectively. Worm gears 329a and 329b provide a 90° change in drive direction and in one embodiment of the present invention provided an 8 to 1 gear reduction.

Other drive/transmission combinations can be used to control the motion of drive members 324a and 324b. For example, a differential system can be provided for the transmission. While one side is driven, the other side can be braked to prevent back drive. A constant variable transmission can be used. A transmission with a solenoid in the injector support base and a driving flex cable (for example, a plastic cable) can be used. An air drive can be provided (for example, in base 382) in controllable fluid connection with at least one at a time of two air motors provided in the injector head. A single ultrasonic motor can be placed in the head, eliminating all the shafting, while using a transmission to allow the single motor (which is expensive and has expensive drive circuitry) to drive one or both syringes. Two motors (for example, Piezo motors) can be provided with a single servo, which is switchable between the motors (see, for example, FIG. 13B). A few of these embodiments are discussed further below.

Injector 310 also provides a novel drive transfer system to transfer drive from motor 386 to transmission 340. In a number of currently available injector systems (for example, as illustrated in FIGS. 1A and 1B), drive is transferred between a motor and a drive member or piston via a flexible shaft. There are a number of problems with use of relatively long flexible shafts, including rigidity/wind-up and back lash. As described above, drive is provided to Sprague clutch system 342 via a rigid drive shaft 344. As illustrated, for example, in FIGS. 4 through 6, a second rigid drive shaft system 360 is provided in operative connection with motor 386. In one embodiment, drive shaft system 360 included a first rigid drive shaft 362 in operative connection with motor 386. A second rigid drive shaft 364 was telescopically, slidably connected to first drive shaft 362 using a non-circular telescopic connection (for example, a hexagonal connection), so that second drive shaft 364 can be telescoped with respect to first drive shaft 362 to, for example, adjust the height of injector head 310, while maintaining an operative connection with motor 386.

Figure 8:
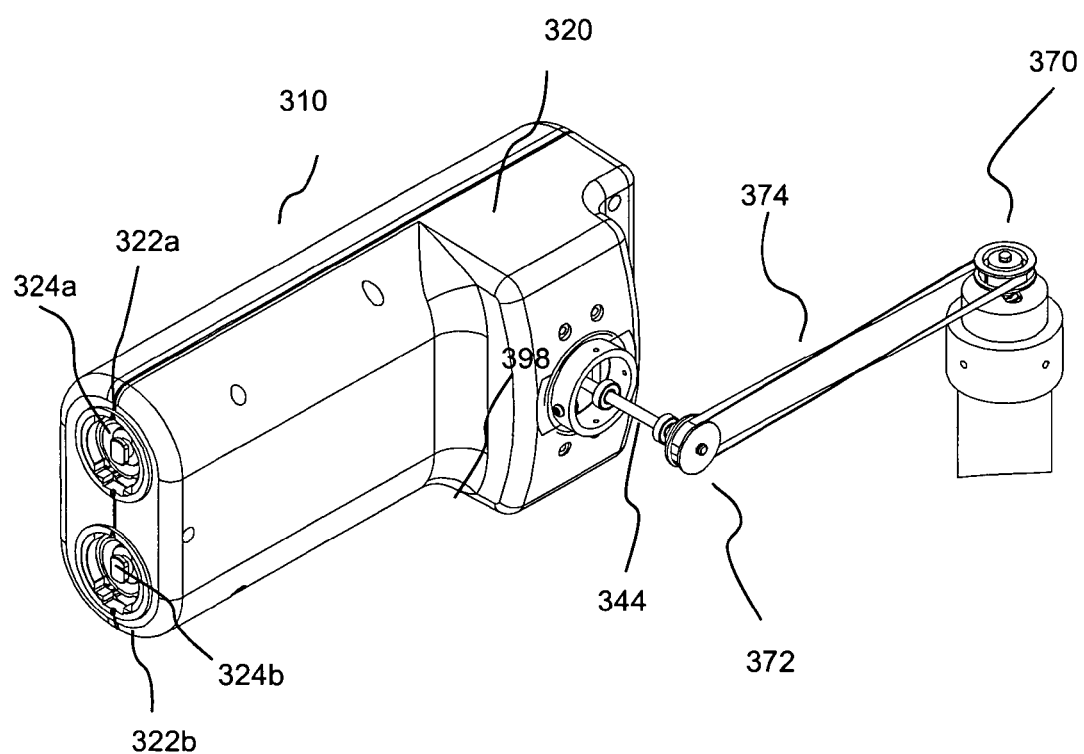
FIG. 8 illustrates a perspective view of the injector head in a position in which a belt of the drive transfer system is twisted.

A flexible connection is provided between drive shaft 364 and drive shaft 342 to transfer drive therebetween. In the embodiment illustrated in, for example, FIGS. 3 through 8, a belt system transfers drive from rigid drive shaft 364 to rigid drive shaft 344. In that regard, drive shaft 364 is connected to a pulley 370. Drive shaft 344 is connected to a pulley 372. A belt 374 is in operative connection between pulley 370 and pulley 372. In one embodiment, each of pulleys 370, 372 and belt 374 included teeth to prevent slippage. As illustrated in FIG. 8, upon rotation of injector head 310 about the axis of generally horizontal member 397, belt 374 twists ¼ turn. The use of drive shafts 360 and 344, connected via a flexible belt connection, eliminates the problems of rigidity and back lash associated with flexible shafts. Indeed, a flexible shaft can be used in the present invention to transfer drive between drive shafts 360 and 344, without introducing significant rigidity or back lash. In that regard, such effects are greatly reduced when flexible shafts of relatively short length (for example, having a length less than 18 inches or less than 12 inches) are used.

Figure 9A:
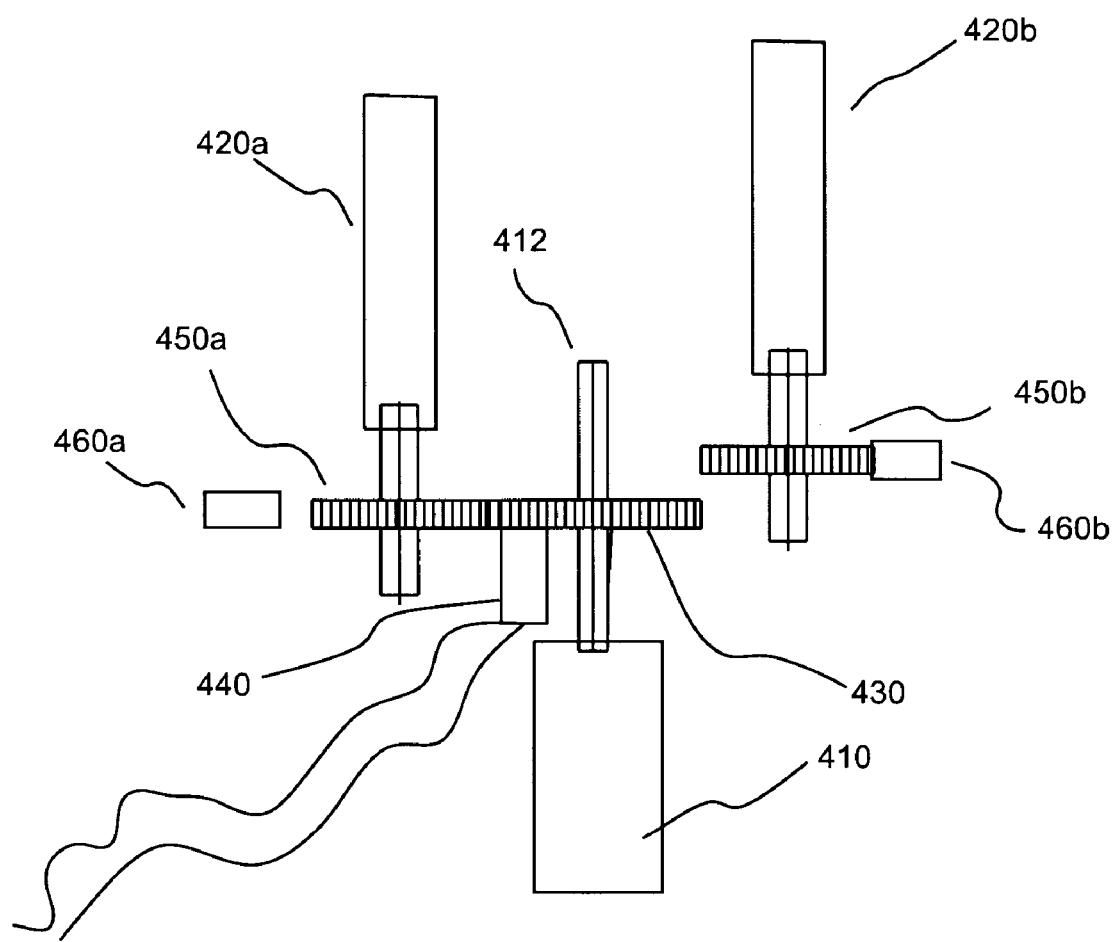
FIG. 9A illustrates an embodiment of a sliding transmission of the present invention.

FIG. 9A illustrates in a schematic fashion how a single drive (for example, a motor drive 410) can be used to drive two ball screws 420a and 420b (and thereby syringe plungers) using an embodiment of a shifting transmission. In this embodiment, motor 410 drive rotates a moving (for example, sliding) gear 430 that can move/slide on motor shaft 412. Adjusting the position of sliding gear 430 (driven by motor 410) via a gear actuator 440 can: (1) engage drive gear 450a to drive ball screw 420a for forward or backward motion of drive ball screw 450a or (2) engage drive gear 450b to drive ball screw 420b for forward or backward motion of drive ball screw 420b.

Additionally, a brake system can alternately be engaged to the drive gear other than the drive gear engaged to sliding gear 430. For example, by moving sliding gear 430 to engage drive gear 450a, it can allow for breaking gear 460b, pawl, ratchet or other braking system to engage with drive gear 450b and push braking gear 460a out of engagement with drive gear 450a (and vice versa when engaging drive gear 450b). The braking gear system can prevent the one of the ball screws not in operative connection with motor 410 from being back driven. Alternative a worm gear can be provided between drive gear 450a and ball screw 420a and/or between drive gear 450b and ball screw 420b.

The gear actuator can, for example, be activated by a solenoid or other device in the base by operating a plastic throttle cable. A Piezo electric activator, a hydraulic actuator, a pneumatic driven actuator, a Tcam actuator (thermal activated wax) or a push pull cable operated by the technician can also be used. Once again, actuators suitable for use in an MR environments are described generally, in U.S. patent application Ser. No. 10/916,946 (filed Aug. 12, 2004) and Ser. No. 10/921,083 (filed Aug. 18, 2004), assigned to the assignee of the present invention, the disclosure of which is incorporated herein by reference.

Figure 9B:
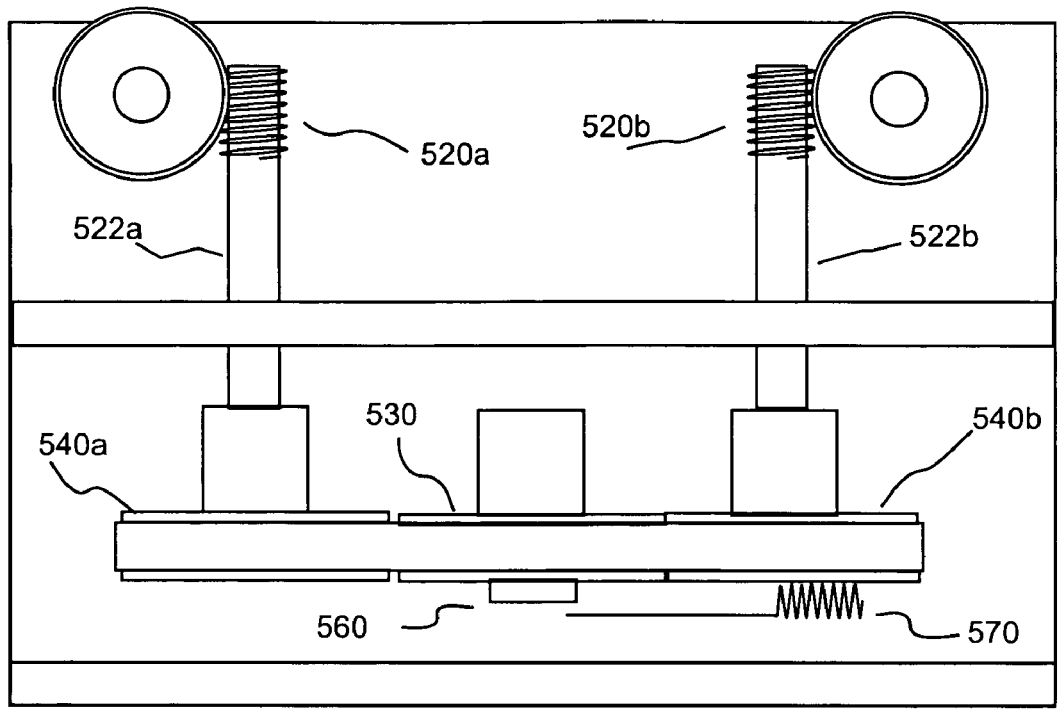
FIG. 9B illustrates a top view of an embodiment of a transmission system of the present invention including a movable gear which is rotatable about an axis parallel to its rotational axis.
Figure 9C:
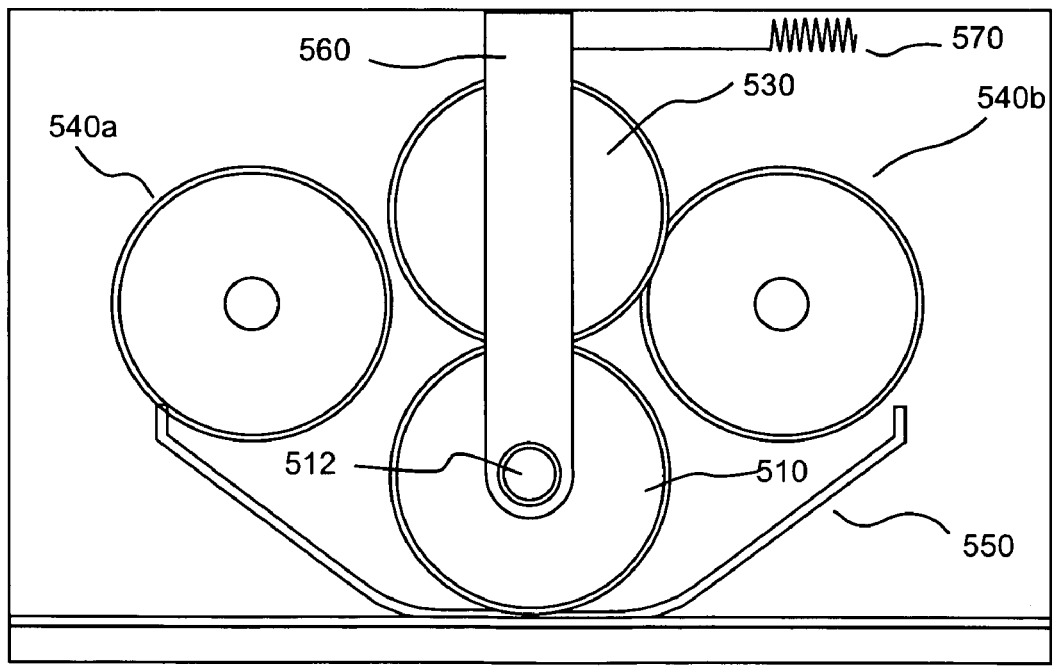
FIG. 9C illustrates a side view of the transmission of FIG. 9B.

FIGS. 9B and 9C illustrate another embodiment of a movable gear transmission system operable to drive two different loads, such as ball screws or lead screws connected to syringe plungers, via worm gears 520a and 520b from a single power source (for example, a motor—not shown) in operative connection with a gear 510 (see FIG. 9C). As described above, it can also be desirable to provide a mechanism to prevent the non-driven load from moving. In the illustrated embodiment, a mechanism is provided to switch drive connections from a common power source capable of driving either of worm gears 520*a* or 520*b* and to provide an automatic securing of the non-driven worm gear (preventing it from rotating). This transmission can be conveniently geared to provide any ratio needed to each worm gear independent of the other worm gear. A center follower gear or drive engagement gear 530 is switched from drive gear 540*a* (which drives worm gear 520*a* via shaft 522*a*) to drive gear 540*b* (which drives worm gear 520*b* via shaft 522*b*) by simply shifting the position of follower gear 530 into engagement with the desired drive gear train. The non-drive gear is automatically secured from moving by, for example, locking the non-driven gear (drive gear 540*a* in FIGS. 9B and 9C) to a locking mechanism (for example, a braking bar 550) engaged into the teeth of the non-driven gear. The locking mechanism does not have to engage the teeth but could be a friction device pressed firmly against the non-connected/non-driven drive gear to prevent undesirable rotation when not driven by the power source. Follower gear 530 is rotated about axis 512 of the power gear shaft (while maintaining its operative connection with powering gear 510) to engage the desired drive gear via operative connection to a lever arm 560 which is rotatable about axis 512. The position of follower gear 530 can be controlled/changed either manual or automatically. In other words it can be switched by hand or some type of, for example, mechanical or electromechanical mechanism such as a servo, solenoid etc. represented schematically as control mechanism 570. Once again, the non-driven drive gear is secured from rotating by braking mechanism 550, and control of the position of breaking mechanism can be associated with the motion that is used to engage the driven gear. The non-driven drive gear is preferably held from movement before follower gear 530 is disengaged, thus ensuring non movement of the non-drive drive gear.

Figure 10A:
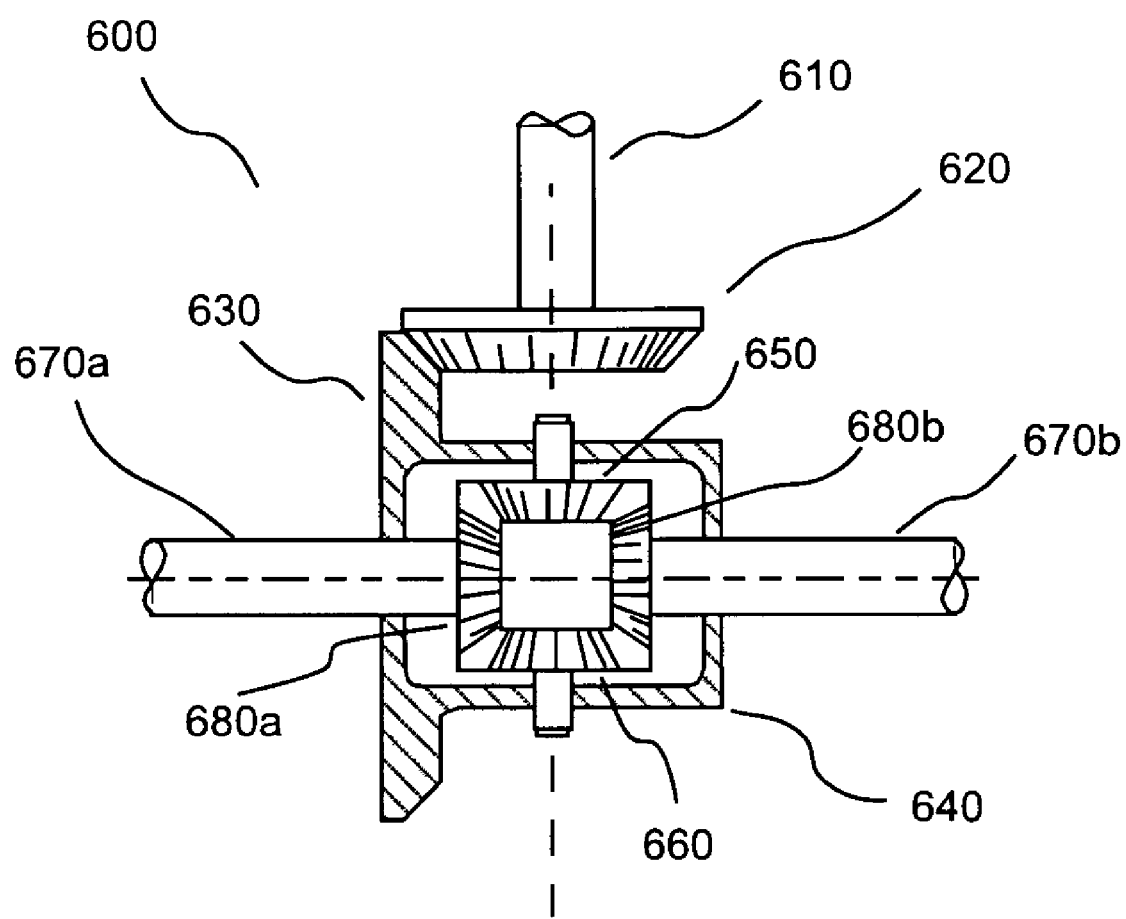
FIG. 10A illustrates an embodiment of a differential transmission of the present invention.

As illustrated in FIGS. 10A and 10B, a single input to a dual output drive differential transmission 600 can also be used in the present invention. In this embodiment, a driveshaft 610 is connected to a power source via gearing/shafts/belts/etc. Driveshaft 610 can be driven forward or reverse. A drive gear 620 in operative connection with drive shaft 610 drives a ring gear 630 and differential housing 640. Spider gears 650 and 660 can rotate within differential housing 640. If both shafts 670*a* and 670 and associated shaft gears 680*a* and 680*b*, respectively, are free to rotate, spider gears 650 and 660 do not. In this scenario, shafts 670*a* and 670*b* turn at the same speed as the ring gear 630/housing 640. If one of shafts 670*a* or 670*b* is stopped, spider gears 650 and 660 turn, causing the other shaft to turn at 2× the speed of ring gear 630. This is the basis of operation of illustrated transmission 600. Transmission 600 can employ a mechanism (for example, one or more brake systems) to allow either shaft 670*a* to turn or shaft 670*b* to turn, but not both. As described above, this embodiment prevents back-drive of the shaft that is stopped. The direction of driveshaft 610 can correlate to the shaft that is allowed to turn (for example, driveshaft 610 driven forward corresponding to shaft 670*a* driven forward and shaft 670*b* stopped/locked). The diagrams of FIG. 10B through 10E illustrate the rotations of shaft 670*a* and shaft 670*b*. Shaft 670*a* and shaft 670*b* can be connected to drive member 324*a* and drive member 324*b*, respectively, via appropriate gearing/shafts/belts/etc. as known in the art.

Figure 11:
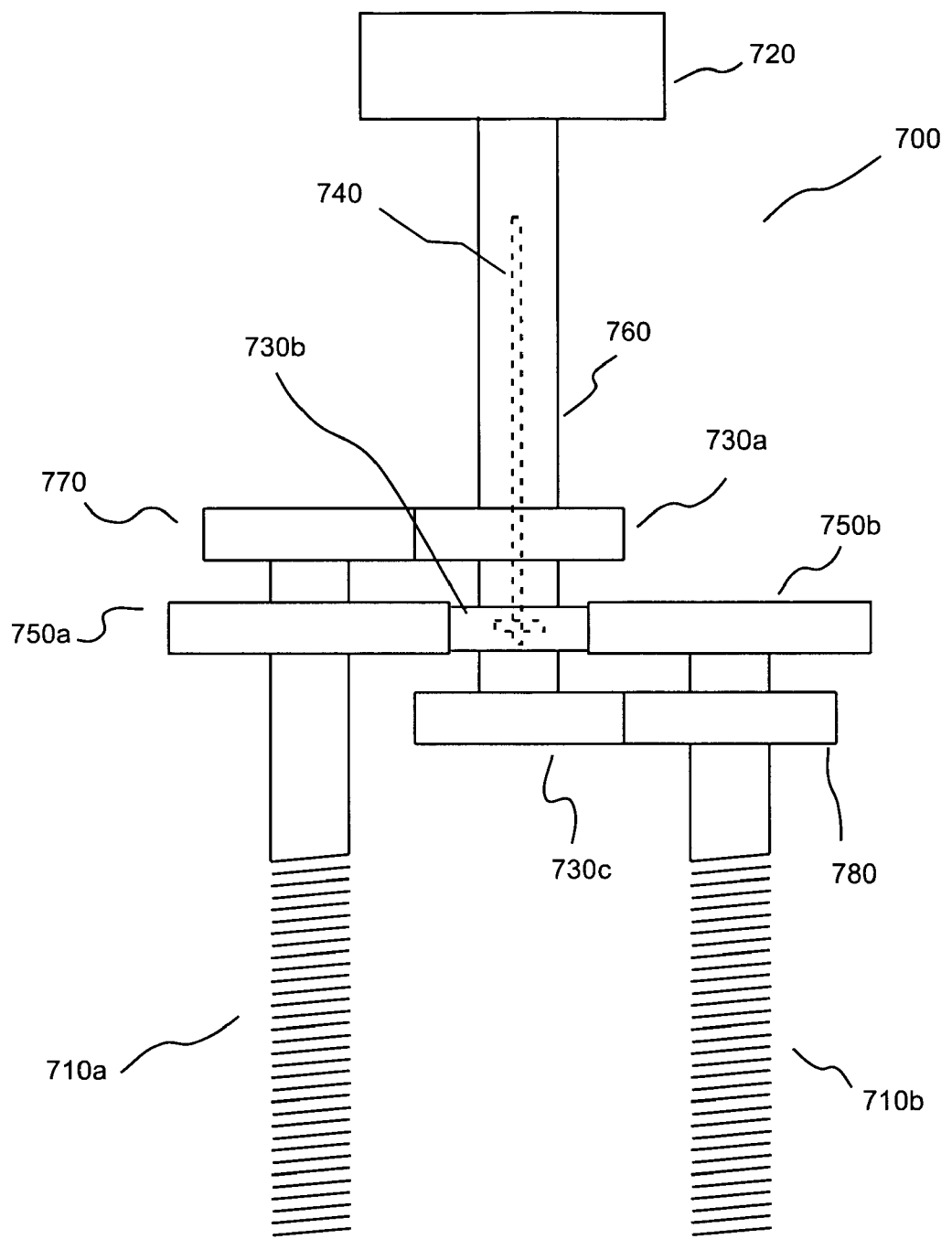
FIG. 11 illustrates an embodiment of a transmission systems of the present invention including variable gear ratios.

FIG. 11 illustrates how injection of fluids from, for example, two different syringes and selectable mixing of fluids from the two syringes can be achieved with the injectors of the present invention through the use of discrete gears and a single power input. In the embodiment of FIG. 11, a system 700 is illustrated wherein the ratio of fluid between fluid A and fluid B can be varied in fixed proportions. As described above, syringe plungers (not shown in FIG. 11) can be driven to inject fluids A and B from syringes (not shown in FIG. 11) via a drive train including balls screws 710*a* and 710*b*. In this simple diagram there are three possible flow ratios: (1) fluid A only (100% fluid A), (2) fluid A/fluid B (50% of each fluid A and fluid B), and (3) fluid B only (100% fluid B). A motor drive 720 rotates in the same direction and turns at the same speed in all cases. Three center driving gears 730*a* (for example, a 48-tooth gear), 730*b* (for example, a 32-tooth gear) and 730*c* (for example, a 48-tooth gear) are selectively coupled to motor 720 via a movable coupler 740 in three selectable positions. For example, in the center position of coupler 740 (illustrated in FIG. 11), driving gear 730*b* (having, for example, 32 teeth) is engaged/driven and both ball screw gears 750*a* and 750*b* (for example, having 64 teeth) are driven. Thus, ball screw gears 750*a* and 750*b* turn at half the speed of the input shaft 760 (resulting in flow of both fluid A and fluid B in a flow ratio of 50% fluid A and 50% fluid B). Driving gears 730*a* and 730*c* are not driven in the center position of coupler 740. The fluid delivery is equal to the rate of input. At the top position of gear selector 740, driving gear 730*a* is engaged/driven to drive ball screw gear 770 (for example, having 48 teeth) and the drive is 48 teeth to 48 teeth. In this state, only ball screw 710*a* turns (resulting in flow of only fluid A or a corresponding flow ratio of 100% fluid A). In the top position, driving gears 730*b* and 730*c* are not driven. At the bottom position of gear selector 740, driving gear 730*c* is engaged/driven to drive ball screw gear 78- and the drive is 48 teeth to 48 teeth. In this state, only ball screw 710*b* turns (resulting in flow of only fluid B or a corresponding flow ratio of 100% fluid B). In the bottom position, driving gears 730*a* and 730*b* are not driven. As clear to one skilled in the art, this embodiment can be expanded to many different mixing ratios by adding additional gears. Control of a gear selector similar in operation to gear selector 740 is discussed below in connection with FIG. 14B through 14E.

Additionally, a constantly variable transmission or CVT as known in the transmission arts can be used to drive both ball screws. In this type of system, as one transmission increases drive ratio on one ball screw it decreases drive ratio on the other ball screw. In this fashion, mixing ratios can be changed. This embodiment is similar to the embodiment described in connection with FIG. 11, wherein the ratio is infinitely changeable from 0% to 100% of either fluid.

Figure 12A:
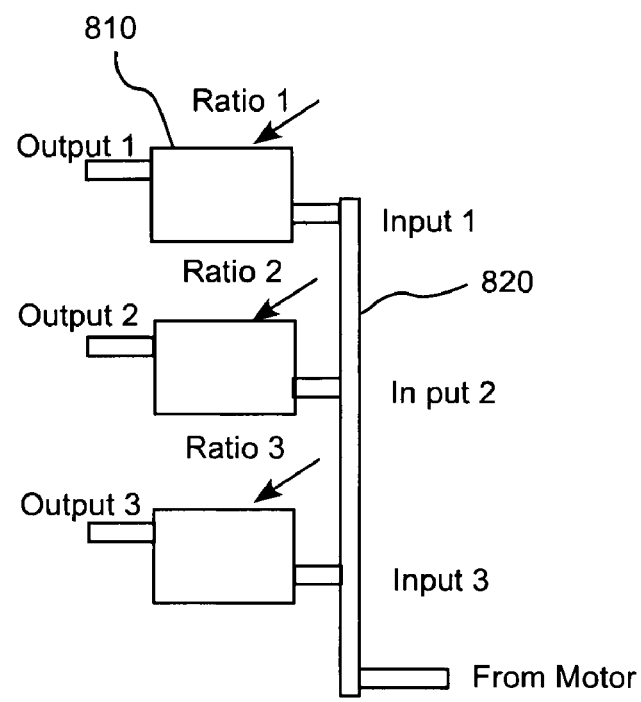
FIG. 12A illustrates an embodiment of use of one or more continuously variable transmissions in the present invention.

As illustrated, for example, in FIG. 12A, two or more continuously variable transmissions (CVTs) 810 and a physical or controlling linkage 820 between CVTs (for example, a shaft with gears or a belt with pulleys) that ensures a constant total flow with a varying ratio of flow can be use. Any of a number of CVTs are suitable for use in the present invention, including friction, ratcheting, and positive drive CVTs as known in the art. Potentially less desirable because of cost, but beneficial because of power capability, are hydrostatic CVTs. The ratio controllers can be mechanical if there are only two outputs. Electrical control can accommodate two or more outputs. Clutches or other selection mechanism can be used to allow input to only the desired CVTs.

Figure 12B:
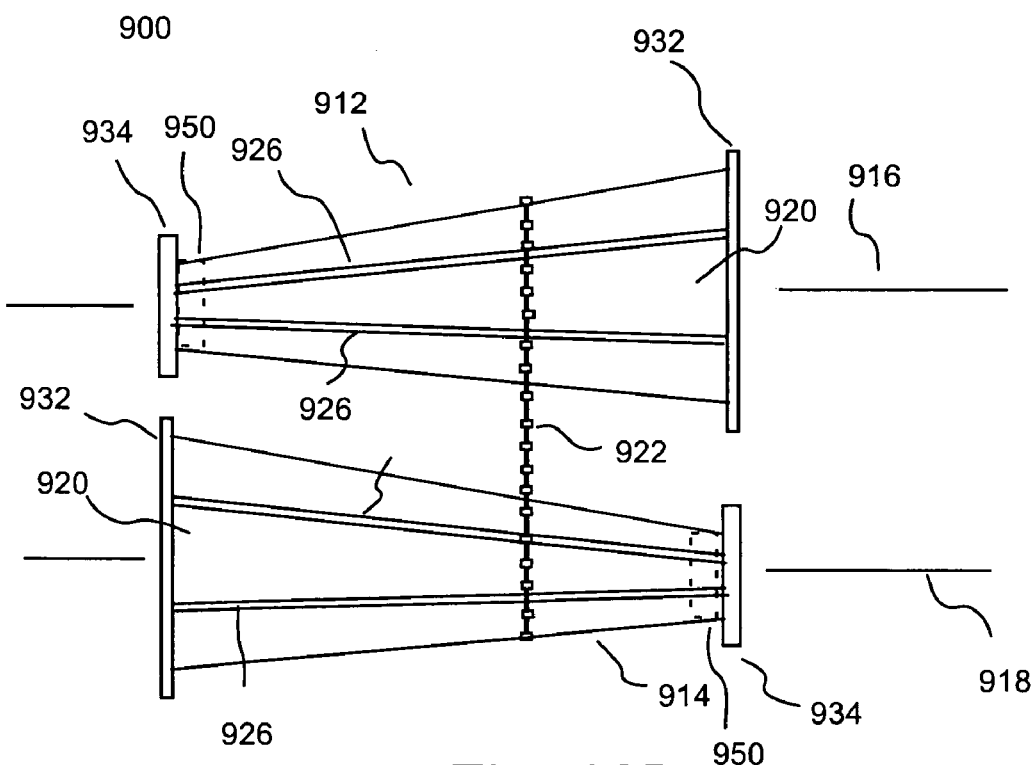
FIG. 12B illustrates an embodiment of one continuously variable transmission for use in the present invention including conical shaped torque elements.

In a representative example of another embodiment of use of a CVT of the present invention, the CVT of U.S. Pat. No. 6,575,856, the disclosure of which is incorporated herein by reference, can be used. An embodiment developed from FIG. 1 of U.S. Pat. No. 6,575,856 is set forth herein as FIG. 12B. In that regard, FIG. 12B illustrates a transmission 900 including pair of conical torque elements in the form rotatable conical sprocket wheel assemblies 912 and 914 that are spaced apart on parallel axes 916 and 918, respectively. The structures of sprocket wheel assemblies 912 and 914 are generally identical in structure and function. Sprocket wheel assemblies 912 and 914 include a truncated cone 920. Power can, for example, be input to the system via primary or driving sprocket wheel 912 and transmitted to secondary driven sprocket wheel 914 via an endless belt or beaded chain assembly 922 which encircles both sprocket wheels 912 and 914. Sprocket wheels 912 and 914 further include axially extending, elongated sprocket bars or cogs 926. Sprocket wheels 912 and 914 also include, at each axial end thereof, ring gears 932 and 934. Ring gears 932 and 934 can be appropriately geared to other internal workings of the transmission so that input torque can be input to the transmission and output torque delivered from the transmission. Alternatively sprocket wheels 912 and 914 can be directly affixed to the transmission input and output shaft.

There are several ways to utilize the CVT of U.S. Pat. No. 6,575,856 in the present invention. For example, the shaft selection mechanism discussed above can be used to selectably drive either shaft connected to conical sprocket wheel assemblies 912 and 914 and situated along axes 916 or 918, respectively. Then, as chain drive 922 is moved from one end to the other, the ratio between the two shafts is controlled. As shown above, both shafts always turn. Normally, CVTs do not include a 0 ratio. To allow just a single fluid to be delivered (corresponding to a 100% to 0% ratio), sprocket bars 926 can be absent from one or both of cones 912 and 914 near narrow end gear 934 thereof, so that there is a region (represented by dashed areas 950 in FIG. 12B) on one or both cones wherein chain drive 922 slides over the cone without rotating it. Thus, if drive chain 922 is moved to that region, only one shaft is driven.

Alternatively, a single drive path from the motor could drive a spline, hexagonal or other slipable rotational structure (not shown) that engages drive chain 922 with a constant drive ratio as it moves back and forth. Moving the position of drive chain 922 would then change the ratio of fluids delivery.

FIG. 13A illustrates an embodiment of a current type of system for injection of two fluids in which two motors (motor A and motor B) operated by two servos (servo A and servo B, respectively). As illustrated in FIG. 13B, motors A and B (for example, Piezo motors) can be provided with a single servo, which is switchable between the motors via a switching device. The switching device can, for example, include multiple pole, double throw contacts to switch all conductor for power and feedback.

Figure 14A:
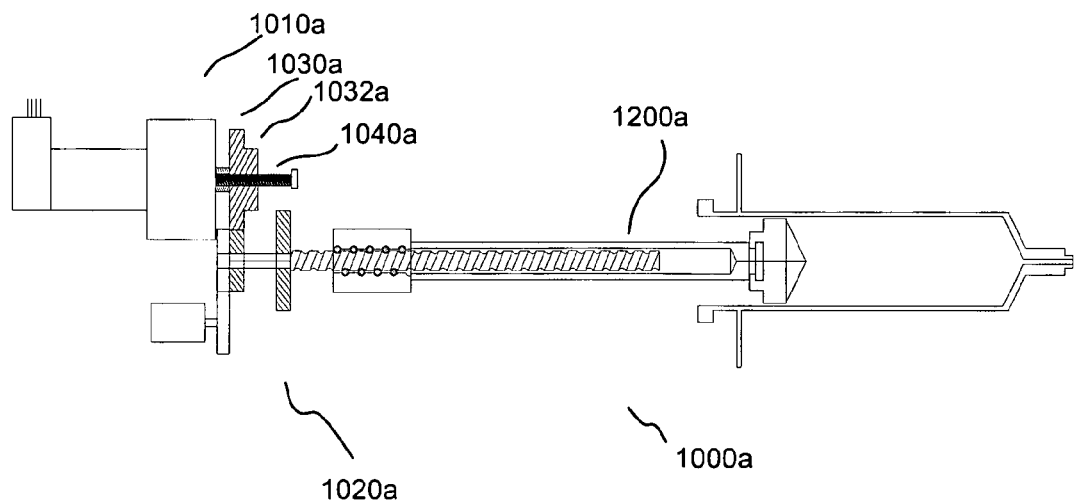
FIG. 14A illustrates a partially cross-sectional view of an embodiment of an injector system of the present invention including a variable speed transmission including a moveable gear selector operable to activate one of a plurality of gears/gear ratios to, for example, provide different speeds in a forward and reverse direction.

FIG. 14A illustrates an embodiment of a drive train system for use, for example, in connection with providing drive to rigid drive shaft 344, other power inputs of the injectors of the present invention and injectors generally. In general, currently available injectors have a motor and a drive that is matched to the requirements of defined fluid injection parameters. The product of the maximum pressure, the flow rate, and the frictional loss determines the motor power. The designer is required to choose a motor that has the capabilities to produce the maximum power output. Problems occur, for example, in that conflicting requirements can arise.

For example, the maximum injection rate for a particular injector can be on the order of 10 ml. per sec. However, in operations such filling the syringe or operating the piston in reverse, the rate is perceived to be too slow. However, increasing the speed of such operations by rotating the motor more quickly may require the motor to exceed the its maximum speed limitations. Further, to use a lower gear ratio to obtain a higher flow rate would require the use of a much larger motor. The latter option would substantially increase cost and take up more volume in a situation wherein space is at a premium.

Another problem occurs in injectors wherein the flow may be set in ml/sec, ml/min, or ml/hr. The required speed ratio can be over 3600:1. It is difficult to design motor and the control circuitry to achieve such a range. A mechanical mechanism to change to a more desired motor speed would facilitate control of the injector.

Figure 14B:
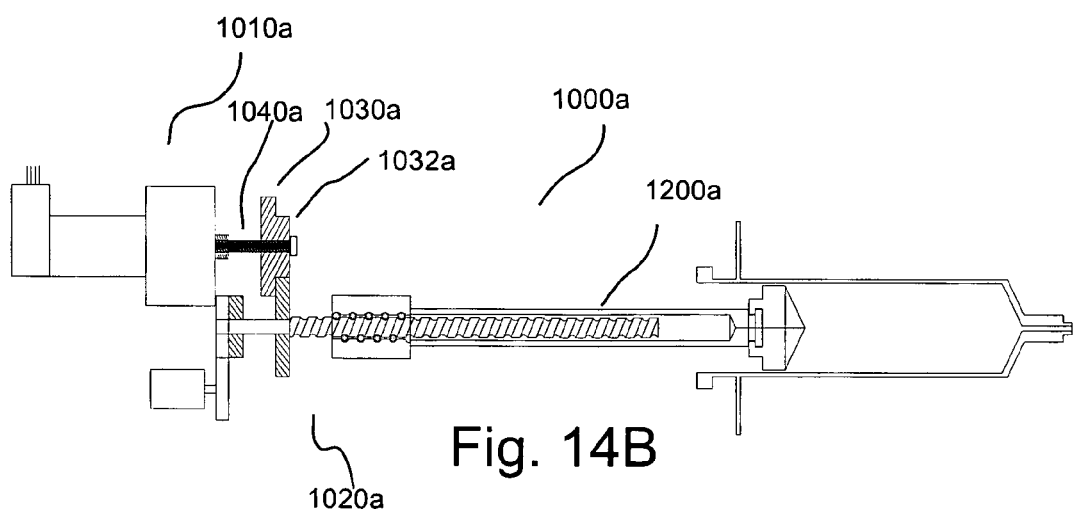
FIG. 14B illustrates the injector system of the present invention with the gear selection shifted forward.

An embodiment of such a system is, for example, illustrated in FIGS. 14A an 14B. The embodiment of FIGS. 14A and 14B is, for example, useful in a case wherein one direction in the movement of the piston is substantially different in force and speed than the other direction. For example, an injector can require a low speed forward with high pressure (for an injection procedure), and also require high speed rearward with relatively low pressure/force.

In system 1000*a* of FIGS. 14A and 14B there are two drives 1010*a* and 1020*a* in spaced parallel relation. The drive gears 1030*a* and 1034*a*' are driven by a helical drive screw 1040*a*. In one direction the gears translates to the stop on one end of the drive, the reverse direction drives it the other side. When the forward direction the drive with a higher gear reduction is automatically used. In the reverse direction a lower reduction is used. With system 1000*a*, a drive member such as piston 1200*a* (or, for example, drive shaft 344 described above) moves faster in reverse than it does moving forward, and is capable of exerting more force when moving forward than when moving in reverse. This result can be achieved without any interaction from the user or the control system. This type of system can be readily reversed in a system that requires a slow speed reverse and a fast speed forward. Moreover, drive ratios can be readily selected to match the requirements of the system.

Figure 14C:
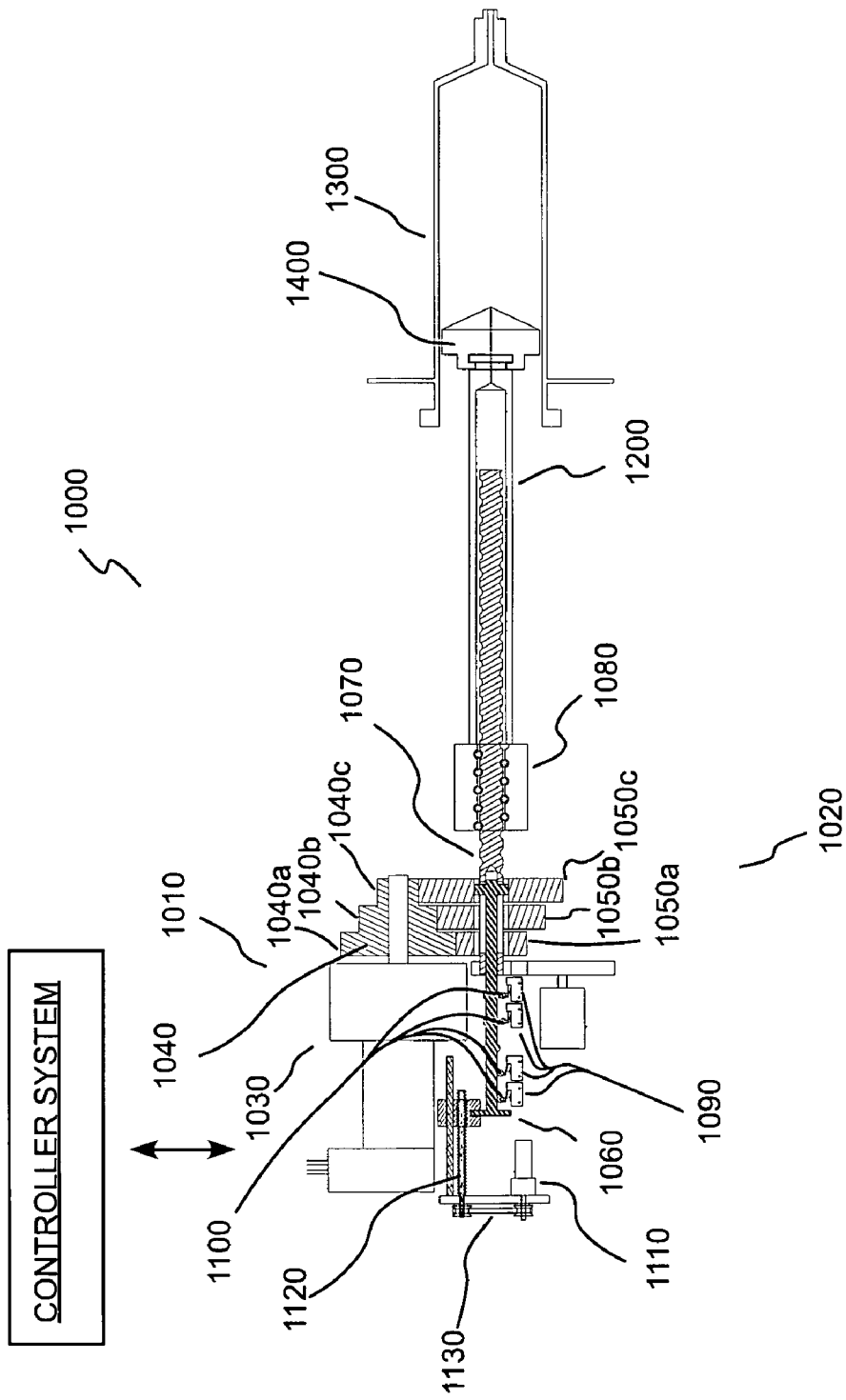
FIG. 14C illustrates a partially cross-sectional view of an embodiment of an injector of the present invention including a variable speed transmission including a moveable gear selector operable to activate one of a plurality of gears/gear ratios.
Figure 14D:
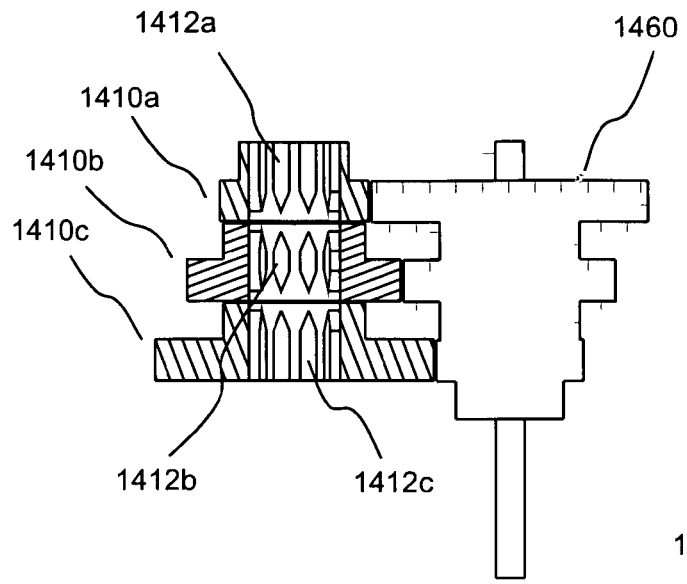
FIG. 14D illustrates a partially side, cross-sectional view of an embodiment of the gears of the transmission of FIG. 14A.

In system 1000 of FIG. 14C there are also two drives 1010 and 1020 in spaced parallel relation. With system 1000, a drive member such as piston 1200 (or, for example, drive shaft 344 described above) is capable of moving at different speeds. This result can be achieved without any interaction from the user or the control system. Suitable drive ratios can be readily selected to match the requirements of the system.

In system 1000, a power source such as a gear motor system 1030 (for example, including an encoder) is operatively connected via a powering motor shaft to a combination gear or step gear 1040. In the illustrated embodiment, combination gear 1040 includes three differently sized gears 1040*a-c* on it. Gears 1040*a*, 1040*b* and 1040*c* of combination gear 1040 mate with (and powers or drives) three gears 1050*a*, 1050*b* and 1050*c*, respectively, which are free to rotate relative to each other. A shift actuator or gear selector 1060 selects one of gears 1050*a*, 1050*b* and 1050*c* to drive a power output such as ball screw 1070. The other two gears are free to rotate as driven by combination gear 1040. Ball screw 1070 eventually drives piston 1200 via a ball nut 1080, which pressurizes fluid when a syringe 1300, via a piston 1310 connected to a syringe plunger 1310 slidably positioned within syringe 1310. In this embodiment, as gear selector 1060 is moved from a forward position (toward ball screw 1070) to a rearward position, ball screw 1070 moves more slowly and motor 1030 can be capable of delivering a higher pressure at a slower rate.

In the illustrated embodiment, gear selector 1060 has three distinct positions. These can be determined by the states of four limit switches 1090, which detect raised lobes 1100 on gear selector or coupler 1060. A shift gear motor 1110, by translation of a threaded shaft 1120 in operative connection with a drive belt 1130, moves gear selector 1060.

The controller system (for example, one or more microprocessor) of the injector determined/establishes the gear ratio. The desired gear ratios can also be established manually. Depending on the desired ratio and the beginning position gear selector 1060, gear motor 1110 turns one direction or the other direction until limit switches 1090 indicate that the proper position associated with a desired gear ration has been achieved. All parameters of the injector can be set to function properly with this drive ratio.

Although a three-speed transmission is illustrate in FIG. 14C, the transmission can be from two speeds to as many speeds as needed (for example, four, five, six speeds etc.). Moreover, ratios set forth in the illustrated embodiment do not necessarily set forth ideal ratios for all applications. If a transmission system such as the one illustrated in FIG. 14C were used for the effecting different speed/force one direction versus the opposite direction, only two speeds may be needed. A ratio of two to one in such an embodiment may be all that is necessary. For an injector system that has speed ranges that are based on different time units (for example, seconds, minutes, hours) the ratios may be higher since the time units are 60 times each other.

FIGS. 14D through 14G illustrate further details of the manner in which an actuator, coupler or gear selector can establish the gear ratio in a transmission as set forth, for example, in FIG. 14A or in FIG. 11. In FIGS. 14D through 14G, gears 1410a, 1410b and 1410c are the selectable drive gears. A driving shaft 1420 holds gears 1410a, 1410b and 1410c. A gear selector shaft, actuator or coupler 1430 is operable to couple drive shaft 1420 to the selected gear via a drive pin 1440. Drive pin 1440 passes through actuator 1430 and extends through a slot 1450 in drive shaft 1420. Each of gears 1410a, 1410b and 1410c includes a drive lug 1412a, 1412b and 1412c, respectively, on an inner diameter thereof. In the illustrated embodiment, there are eight lugs per gear. Drive lugs 1412a, 1412b and 1412c can include leads (for example, tapered surfaces—see, for example, FIG. 14D) thereon to facilitate in aligning the gear to drive pin 1440 when a different ratio is selected via repositioning of actuator shaft 1430 and connected drive pin 1440.

Figure 14E:
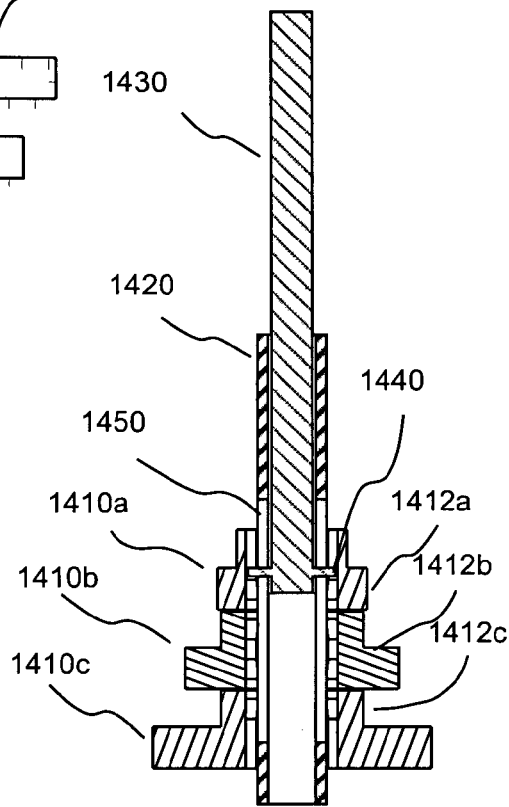
FIG. 14E illustrates a side, cross-sectional view of the moveable gear selector in operative connection with one of the drive gears of FIG. 14B.
Figure 14F:
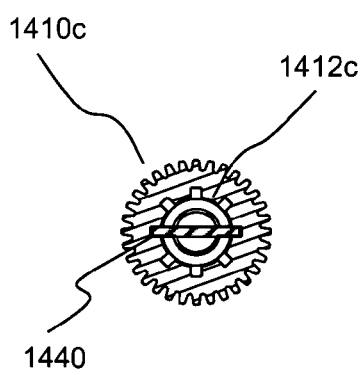
FIG. 14F illustrates a top, cross-sectional view of one of the drive gears of FIG. 14B.
Figure 14G:
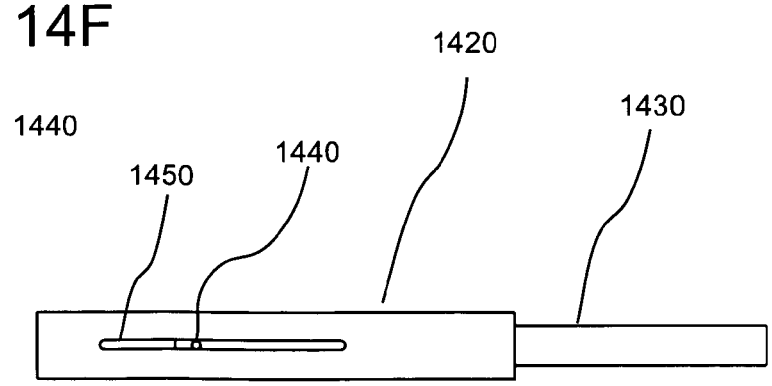
FIG. 14G illustrates an embodiment of the drive shaft of FIG. 14C with the gear selector slideably positioned within an axial bore thereof.

Gears 1410a, 1410b and 1410c are all on shaft 1420 and are all free to rotate relative to shaft 1420 when not in operative connection with drive pin 1440. Gears 1410a, 1410b and 1410c rotate at different rates each mates with one of three corresponding gears (of different sizes) on a combination gear 1460. When gear selector 1430 is moved inside the bore of drive shaft 1420, drive pin 1440 slides within slot 1450. When drive pin 1440 is centered on one of drive lugs 1412a, 1412b and 1412c, the selected gear is driven. In FIG. 14E, drive pin 1440 is shown in operative connection with drive lug 1412a of drive gear 1410a.

Although the present invention has been described in detail in connection with the above embodiments and/or examples, it should be understood that such detail is illustrative and not restrictive, and that those skilled in the art can make variations without departing from the invention. The scope of the invention is indicated by the following claims rather than by the foregoing description. All changes and variations that come within the meaning and range of equivalency of the claims are to be embraced within their scope.

What is claimed is:

1. An injector for injecting a fluid into a patient, comprising:
    (a) a first pressurizing mechanism adapted to operatively connect with a first syringe to pressurize a fluid therein;
    (b) a second pressurizing mechanism adapted to operatively connect with a second syringe to pressurize a fluid therein;
    (c) a single drive; and
    (d) a transmission to control how power from the single drive is distributed to the first pressurizing mechanism of the first syringe and to the second pressurizing mechanism of the second syringe to control injection of fluid from the first syringe and from the second syringe, the transmission having a first one way clutch gear and a second one way clutch gear spaced from each other on and in operative connection with a drive shaft that is in operative connection with the single drive such that (I) the first one way clutch gear is driven by the drive shaft upon rotation of the drive shaft in a first direction and slipping upon rotation of the drive shaft in a second direction opposite the first direction and (II) the second one way clutch gear is driven by the drive shaft upon rotation of the drive shaft in the second direction and slipping upon rotation of the drive shaft in the first direction; wherein the first one way clutch gear and the second one way clutch gear are linearly movable on the drive shaft.

2. The injector of claim 1 wherein the transmission is a mechanical transmission with no active electronic actuators.

3. The injector of claim 2 wherein the transmission is fabricated from MR compatible components.

4. The injector of claim 1 wherein the first pressurizing mechanism is a first drive member adapted to operatively connect with a first plunger slidably disposed within the first syringe, and wherein the second pressurizing mechanism is a second drive member adapted to operatively connect with a second plunger slidably disposed within the second syringe.

5. The injector of claim 4 wherein the first drive member is in operative connection with a first ball screw that is adapted to be in operative connection with the single drive and the second drive member is adapted to be in operative connection with a second ball screw that is in operative connection with the single drive.

6. The injector of claim 5 wherein the first drive member is placed in connection with the transmission via a first worm gear and the second drive member is placed in connection with the transmission via a second worm gear.

7. The injector of claim 5 wherein at least one brake system is provided to prevent rearward movement of at least one of the first drive member and the second drive member when the at least one of the first drive member and the second drive member is not being moved by the transmission.

8. The injector of claim 4 wherein at least one brake system is provided to prevent rearward movement of at least one of the first drive member and the second drive member when at least one of the first drive member and the second drive member is not being moved by the transmission.

9. The injector of claim 1 wherein the single drive is a motor.

10. The injector of claim 4 wherein the single drive is a motor.

11. The injector of claim 4 wherein the single drive is connected to a first rigid drive shaft, the first drive shaft being in operative connection with a flexible transfer mechanism for transferring power from the first rigid drive shaft at a first end of the flexible transfer mechanism, the flexible transfer mechanism being in operative connection with a second rigid drive shaft at a second end of the flexible transfer mechanism.

12. The injector of claim 11 wherein the flexible transfer mechanism comprises a belt.

13. The injector of claim 12 wherein the flexible transfer mechanism further comprises a first pulley in operative connection with the first rigid drive shaft and a second pulley in operative connection with the second rigid drive shaft, the first pulley being operatively connected with the second pulley by the belt.

14. The injector of claim 12 wherein the flexible transfer mechanism further comprises a bevel gear and shaft.

15. The injector of claim 11 wherein the flexible transfer mechanism is no greater than 18 inches in length.

16. The injector of claim 11 wherein the flexible transfer mechanism is no greater than 12 inches in length.

17. The injector of claim 13 wherein the first rigid drive shaft includes a first rigid drive shaft member and a second rigid drive shaft member, the second rigid drive shaft member being telescopically connected to the first rigid drive shaft member so that the length of the first rigid drive shaft can be adjusted, the first pulley being in operative connection with the second rigid drive shaft member.

18. The injector of claim 11 wherein the flexible transfer mechanism is a flex shaft.

19. The injector of claim 1 wherein reversal of the motion of the drive causes power to be shifted from the first pressurizing mechanism to the second pressurizing mechanism.

20. The injector of claim 1 wherein when the first one way clutch gear and the second one way clutch gear are in a first position on the drive shaft, the first one way clutch gear is in operative connection with a first gear which is in operative connection with a the first pressurizing mechanism and the second one way clutch gear is in operative connection with a second gear which is in operative connection with the second pressurizing mechanism.

21. The injector of claim 20 wherein when the first one way clutch gear and the second one way clutch gear are in a second position on the drive shaft, the first one way clutch gear is in operative connection with the second gear and the second one way clutch gear is in operative connection with a third gear which is in operative connection with the first pressurizing mechanism, the first gear and the third gear rotating about the same axis.

22. The injector of claim 21 wherein rotation of the first gear or the third gear rotates a first worm gear shaft upon which the first gear and the third gear are positioned and rotation of the second gear rotates a second worm gear shaft upon which the second gear is positioned.

23. The injector of claim 21 further comprising at least one switching system operable to change the position of the first one way clutch gear and the second one way clutch gear on the drive shaft between the first position and the second position, the switching system comprising a signal communicator adapted to send a signal to the single drive to control a direction of rotation of the drive shaft to correspond to a state of the switching system.

24. The injector of claim 23 wherein the switching system comprises a first reverse switch operable when actuated to place the first one way clutch gear and the second one way clutch gear in the second position on the drive shaft, the signal communicator adapted to send a signal to the single drive upon actuation of the first reverse switch to cause rotation of the drive shaft in a first direction to cause rearward motion of the first pressurizing mechanism, and a second reverse switch operable when actuated to position the first one way clutch gear and the second one way clutch gear in the second position on the drive shaft, the signal communicator adapted to send a signal to the drive upon actuation of the second reverse switch to cause rotation of the drive shaft in the second first direction to cause rearward motion of the second pressurizing mechanism.

\* \* \* \* \*

UNITED STATES PATENT AND TRADEMARK OFFICE
CERTIFICATE OF CORRECTION

| | |
|---|---|
| PATENT NO. | : 7,670,315 B2 |
| APPLICATION NO. | : 11/336150 |
| DATED | : March 2, 2010 |
| INVENTOR(S) | : Cowan et al. |

It is certified that error appears in the above-identified patent and that said Letters Patent is hereby corrected as shown below:

IN THE SPECIFICATION
In Column 2, Line 61, delete "driven" and insert -- driven. --, therefor.
In Column 8, Line 64, delete "system system" and insert -- system --, therefor.

IN THE CLAIMS
In Column 21, Line 29, in Claim 20, delete "a the" and insert -- the --.

Signed and Sealed this

Twenty-fourth Day of August, 2010

David J. Kappos
*Director of the United States Patent and Trademark Office*